(12) United States Patent
Nomura et al.

(10) Patent No.: US 11,492,369 B2
(45) Date of Patent: Nov. 8, 2022

(54) METHOD FOR PRODUCING PEPTIDE, AND METHOD FOR PROCESSING BASES

(71) Applicant: Chugai Seiyaku Kabushiki Kaisha, Tokyo (JP)

(72) Inventors: Kenichi Nomura, Shizuoka (JP); Ryuichi Takeyama, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/771,335

(22) PCT Filed: Dec. 14, 2018

(86) PCT No.: PCT/JP2018/046021
§ 371 (c)(1),
(2) Date: Jun. 10, 2020

(87) PCT Pub. No.: WO2019/117274
PCT Pub. Date: Jun. 20, 2019

(65) Prior Publication Data
US 2020/0339623 A1 Oct. 29, 2020

(30) Foreign Application Priority Data
Dec. 15, 2017 (JP) .............................. JP2017-240180

(51) Int. Cl.
*C07K 1/06* (2006.01)
(52) U.S. Cl.
CPC .................................... *C07K 1/063* (2013.01)
(58) Field of Classification Search
CPC .......... C07K 1/063; C07K 1/02; C07K 1/026; C07K 7/64; Y02P 20/55
See application file for complete search history.

(56) References Cited

U.S. PATENT DOCUMENTS

| | | | |
|---|---|---|---|
| 4,859,736 A | 8/1989 | Rink | |
| 5,057,415 A | 10/1991 | Schuetz et al. | |
| 5,059,679 A | 10/1991 | Yajima et al. | |
| 7,288,372 B2 | 10/2007 | Olejnik et al. | |
| 7,439,222 B2 | 10/2008 | Guinn et al. | |
| 8,518,666 B2 | 8/2013 | Wang et al. | |
| 8,809,280 B2 | 8/2014 | Strom et al. | |
| 9,133,245 B2 | 9/2015 | Gao et al. | |
| 9,409,952 B2 | 8/2016 | Kariyuki et al. | |
| 9,701,993 B2 | 7/2017 | Suga et al. | |
| 10,711,268 B2 | 7/2020 | Murakami et al. | |
| 2003/0219780 A1 | 11/2003 | Olejnik et al. | |
| 2008/0044854 A1 | 2/2008 | Wang et al. | |
| 2008/0221303 A1 | 9/2008 | Katzhendler et al. | |
| 2010/0137561 A1 | 6/2010 | Chen | |
| 2010/0292435 A1 | 11/2010 | Chen et al. | |
| 2013/0035296 A1 | 2/2013 | Strom et al. | |
| 2013/0217599 A1 | 8/2013 | Suga et al. | |
| 2014/0194369 A1 | 7/2014 | Gao et al. | |
| 2015/0080549 A1 | 3/2015 | Kariyuki et al. | |
| 2015/0218221 A1 | 8/2015 | Van Der Laan et al. | |
| 2016/0272964 A1 | 9/2016 | Murakami et al. | |
| 2016/0311858 A1 | 10/2016 | Kariyuki et al. | |
| 2018/0127761 A1 | 5/2018 | Ohta et al. | |
| 2019/0338050 A1 | 11/2019 | Nakano et al. | |
| 2020/0040372 A1 | 2/2020 | Tanaka et al. | |
| 2020/0131669 A1 | 4/2020 | Muraoka et al. | |
| 2020/0277327 A1 | 9/2020 | Nomura et al. | |
| 2021/0087572 A1 | 3/2021 | Ohta et al. | |

FOREIGN PATENT DOCUMENTS

| | | |
|---|---|---|
| EP | 1277755 A1 | 1/2003 |
| EP | 1424395 A1 | 6/2004 |
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2647720 A1 | 10/2013 |
| EP | 2813512 A1 | 12/2014 |
| EP | 2492344 B1 | 4/2016 |
| EP | 3031915 A1 | 6/2016 |
| EP | 2141175 B1 | 7/2016 |
| EP | 2813512 B1 | 3/2021 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |

(Continued)

OTHER PUBLICATIONS

Chen et al [Amino Acids, 2014, 46, 367-374] (Year: 2014).*
Office Action dated Jul. 16, 2021 in U.S. Appl. No. 16/619,014, filed Dec. 3, 2019, Muraoka, T. et al.
U.S. Appl. No. 17/024,944, filed Sep. 18, 2020, Ohta, et al.
U.S. Appl. No. 17/291,099, 371(c) date May 4, 2021, Ishizawa.
U.S. Appl. No. 17/297,231, 371(c) date May 26, 2021, Iwasaki, et al.
U.S. Appl. No. 17/312,296, 371(c) date Jun. 9, 2021, Muraoka, et al.

(Continued)

*Primary Examiner* — Sudhakar Katakam
(74) *Attorney, Agent, or Firm* — Nixon & Vanderhye P.C.

(57) ABSTRACT

It was found that a salt formed of an acid and a base having characteristics set forth below can inactivate a deprotecting agent, thereby suppressing redundant peptide elongation:
  (i) the base is different in type from a base used as a deprotecting agent, and
  (ii) a conjugate acid of the base has a pKa smaller than that of a conjugate acid of a base used as a deprotecting agent.

23 Claims, No Drawings

(56) References Cited

FOREIGN PATENT DOCUMENTS

| | | |
|---|---|---|
| JP | H01222795 A | 6/1989 |
| JP | H01250396 A | 10/1989 |
| JP | H0259146 B2 | 12/1990 |
| JP | H0681759 B2 | 10/1994 |
| JP | 2001048866 A | 2/2001 |
| JP | 2003508408 A | 3/2003 |
| JP | 2003531199 A | 10/2003 |
| JP | 2005095013 A | 4/2005 |
| JP | 2007319064 A | 12/2007 |
| JP | 2008125396 A | 6/2008 |
| JP | 2009096791 A | 5/2009 |
| JP | 2009528824 A | 8/2009 |
| JP | 4490663 B2 | 6/2010 |
| JP | 4502293 B2 | 7/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5592893 B2 | 9/2014 |
| JP | 5808882 B2 | 11/2015 |
| JP | 2018509172 A | 4/2018 |
| WO | WO-9831700 A1 | 7/1998 |
| WO | WO-0181325 A2 | 11/2001 |
| WO | WO-02085923 A2 | 10/2002 |
| WO | WO-03014354 A1 | 2/2003 |
| WO | WO 03068990 A1 | 8/2003 |
| WO | WO-03089454 A2 | 10/2003 |
| WO | WO 2005063791 A2 | 7/2005 |
| WO | WO 2007066627 A1 | 6/2007 |
| WO | WO 2007103307 A2 | 9/2007 |
| WO | WO-2007120614 A2 | 10/2007 |
| WO | WO-2008117833 A1 | 10/2008 |
| WO | WO-2010053050 A1 | 5/2010 |
| WO | WO-2010062590 A2 | 6/2010 |
| WO | WO 2010063604 A1 | 6/2010 |
| WO | WO 2010125079 A2 | 11/2010 |
| WO | WO-2011049157 A1 | 4/2011 |
| WO | WO-2011051692 A1 | 5/2011 |
| WO | WO-2011058122 A1 | 5/2011 |
| WO | WO 2012026566 A1 | 3/2012 |
| WO | WO-2012033154 A1 | 3/2012 |
| WO | WO-2012074130 A1 | 6/2012 |
| WO | WO-2012122059 A1 | 9/2012 |
| WO | WO 2013100132 A1 | 7/2013 |
| WO | WO-2014033466 A1 | 3/2014 |
| WO | WO-2014181888 A1 | 11/2014 |
| WO | WO-2015019192 A2 | 2/2015 |
| WO | WO 2015019999 A1 | 2/2015 |
| WO | WO-2015155676 A1 | 10/2015 |
| WO | WO-2015179434 A1 | 11/2015 |
| WO | WO 2015185162 A1 | 12/2015 |
| WO | WO-2016115168 A1 | 7/2016 |
| WO | WO 2016148044 A1 | 9/2016 |
| WO | WO-2016154675 A1 | 10/2016 |
| WO | WO 2017150732 A1 | 9/2017 |
| WO | WO-2017181061 A1 | 10/2017 |
| WO | WO-2018100561 A1 | 6/2018 |
| WO | WO 2018143145 A1 | 8/2018 |
| WO | WO 2018225851 A1 | 12/2018 |
| WO | WO-2018225864 A1 | 12/2018 |
| WO | WO-2020095983 A1 | 5/2020 |
| WO | WO-2020111238 A1 | 6/2020 |
| WO | WO-2020122182 A1 | 6/2020 |
| WO | WO-2020138336 A1 | 7/2020 |
| WO | WO2020189540 A1 | 9/2020 |

OTHER PUBLICATIONS

U.S. Appl. No. 17/417,822, 371(c) date Jun. 24, 2021, Shinohara, et al.
Abdalla, M.A., et al., "Natural Cyclic Peptides as an Attractive Modality for Therapeutics: A Mini Review," Molecules, 23(8):2080 (2018).
Afonso, A., et al., "Solid-Phase Synthesis of Biaryl Cyclic Peptides Containing a 3-Aryltyrosine," Eur J Org Chem., 31:6204-6211 (2012).
Alakhov, Y. B., et al., "Butylation of the Tryptophan Indole Ring: a Side Reaction During the Removal of t-Butyloxycarbonyl and t-Butyl Protecting Groups in Peptide Synthesis," J Chem Soc D., 7:406b-407 (1970).
Alex, A., et al., "Intramolecular hydrogen bonding to improve membrane permeability and absorption in beyond rule of five chemical space," Med Chem Commun., 2:669-674 (2011).
Alvaro, G., et al., "A Novel Activity of Immobilized Penicillin G Acylase: Removal of Benzyloxycarbonyl Amino Protecting Group," Biocatalysis and Biotransformation, 18(3):253-238 (2000).
Bastiaans, H. M. M., et al., "Flexible and Convergent Total Synthesis of Cyclotheonamide B," J Org Chem., 62:3880-3889 (1997).
Bockus, A. T., et al., "Form and Function in Cyclic Peptide Natural Products: A Pharmacokinetic Perspective," Curr Top Med Chem., 13:821-836 (2013).
Bolek, S. and Ignatowska, J., "Ring opening reactions of cyclic sulfamidates. Synthesis of β-fluoroaryl alanines and derivatives of 4,4-difluoroglutamic acid," Journal of Fluorine Chemistry, 27:13-21 (2019).
Brunner, J., "Biosynthetic Incorporation of Non-natural Amino Acids into Proteins," Chemical Society Reviews, 22(3):183-189 (1993).
Burkholder, T. P., et al., "Acid-Catalyzed O-Allylation of β-Hydroxy-α-Amino Acids: an Entry into Conformationally Constrained Dipeptide Surrogates," Bioorganic & Medicinal Chemistry Letters, 2(6):579-582 (1992).
Chen, C.C., et al., "A Mild Removal of Fmoc Group Using Sodium Azide," Amino Acids, 46(2):367-374 (2014).
Chen, J.F., et al., "Effect of Alanine-293 Replacement on the Activity, ATP Binding, and Editing of *Escherichia coli* Leucyl-tRNA Synthetase," Biochemistry 40(5):1144-1149 (2001).
Chen, S., et al., "Structurally Diverse Cyclisation Linkers Impose Different Backbone Conformations in Bicyclic Peptides," Chembiochem., 13(7):1032-1038 (2012).
Coppins, R.L., "Cyclic Antibiotic Peptide Design: Structure and Membrane Interaction," Cyclic Antibiotic Peptide Design: Structure and Membrane Interaction, pp. 1-8 (2001).
Cornella, J., et al., "Practical Ni-Catalyzed Aryl-Alkyl Cross-Coupling of Secondary Redox-Active Esters," J Am Chem Soc., 138:2174-2177 (2016).
Cox, A. D., et al., "Drugging the undruggable RAS: Mission Possible?" Nat Rev Drug Discov., 13:828-851 (2014).
Creighton, C. J., et al., "Mechanistic Studies of an Unusual Amide Bond Scission," J Am Chem Soc., 121:6786-6791 (1999).
Cudic, M. and Fields, G. B., "Solid-Phase Peptide Synthesis," Molecular Biomethods Handbook, 515-545 (2008).
Cusack, S., et al., "The 2 A Crystal Structure of Leucyl-tRNA Synthetase and Its Complex With a Leucyl-Adenylate Analogue," The EMBO Journal, 19(10):2351-2361 (2000).
Dailler, D., et al., "Divergent Synthesis of Aeruginosins Based on a C(sp$^3$)-H Activation Strategy," Chem Eur J., 21:9370-9379 (2015).
Dawson, P.E., et al., "Synthesis of Proteins by Native Chemical Ligation," Science 266(5186):776-779 (1994).
Doublie, S., et al., "Tryptophanyl-tRNA Synthetase Crystal Structure Reveals an Unexpected Homology to Tyrosyl-tRNA Synthetase," Structure 3(1):17-31 (1995).
Falanga, A., et al., "Cyclic Peptides as Novel Therapeutic Microbicides: Engineering of Human Defensin Mimetics," Molecules, 22(7):1217 (2017).
Frankel, A., et al., "Encodamers: Unnatural Peptide Oligomers Encoded in RNA," Chemistry & Biology, 10(11):1043-1050 (2003).
Fujii, N., et al., "Trimethylsilyl Trifluoromethanesulphonate as a Useful Deprotecting Reagent in Both Solution and Solid Phase Peptide Syntheses," J Chem Soc Chem Commun., 4:274-275 (1987).
Fujino, M., et al., "Further Studies of the Use of Multi-substituted Benzenesulfonyl Groups for Protection of the Guanidino Function of Arginine," Chem Pharm Bull., 29(10):2825-2831 (1981).
Fukai, S., et al., "Mechanism of Molecular Interactions for tRNA(Val) Recognition by Valyl-tRNA Synthetase," RNA, 9(1):100-111 (2003).

(56) References Cited

OTHER PUBLICATIONS

Fukai, S., et al., "Structural Basis for Double-Sieve Discrimination of L-Valine From L-Isoleucine and L-Threonine by the Complex of tRNA(Val) and Valyl-tRNA Synthetase," Cell, 103(5):793-803 (2000).
Fukunaga, R. and Yokoyama, S., "Structural Basis for Non-Cognate Amino Acid Discrimination by the Valyl-tRNA Synthetase Editing Domain," The Journal of Biological Chemistry, 280(33):29937-29945 (2005).
Ganesan, A., "The Impact of Natural Products Upon Modern Drug Discovery," Current Opinion in Chemical Biology, 12(3):306-317 (2008).
Genbank, "Valine—tRNA ligase [*Thermus thermophilus*]," Accession No. P96142, accessed on Jan. 27, 2021.
Gilon, C., et al., "Backbone Cyclization: A New Method for Conferring Conformational Constraint on Peptides," Biopolymers, 31(6):745-750 (1991).
Goto, et al., Kagaku Kogyo, 58(4):255-62 (2007).
Goto, Y. and Suga, H., "Translation Initiation With Initiator tRNA Charged With Exotic Peptides," Journal of the American Chemical Society, 131(14):5040-5041 (2009).
Goto, Y., et al., "Flexizymes for Genetic Code Reprogramming," Nature Protocols, 6(6):779-790 (2011).
Gracia, S.R., et al., "Synthesis of Chemically Modified Bioactive Peptides: Recent Advances, Challenges and Developments for Medicinal Chemistry," Future Medicinal Chemistry, 1(7):1289-1310 (2009).
Gravestock, D., et al., "Novel branched isocyanides as useful building blocks in the Passerini-amine deprotection-acyl migration (PADAM) synthesis of potential HIV-1 protease inhibitors," Tetrahedron Letters, 53(26):3225-3229 (2012).
Grosjean, H. and Björk, G. R., "Enzymatic conversion of cytidine to lysidine in anticodon of bacterial tRNA$^{Ile}$—an alternative way of RNA editing," TRENDS Biochem Sci., 29(4):165-168 (2004).
Hartman, M.C., et al., "Enzymatic Aminoacylation of tRNA With Unnatural Amino Acids," Proceedings of the National Academy of Sciences of the United States of America, 103(12):4356-4361 (2006).
Hayashi, G., et al., "Ribosomal Synthesis of Nonstandard Cyclic Peptides and Its Application to Drug Discovery," The Journal of Japanese Biochemical Society, 82(6):505-514 (2010).
Heinis, C., et al., "Phage-Encoded Combinatorial Chemical Libraries Based on Bicyclic Peptides," Nature Chemical Biology 5(7):502-507 (2009).
Higuchi, T. and Suga, H., "Programmed Synthesis of Natural Product-Like Non-Standard Peptides Using the Translation System and Its Application," Journal of Synthetic Organic Chemistry, 68(3):217-227 (2010).
Hoogenboom, H.R., "Selecting and Screening Recombinant Antibody Libraries," Nature Biotechnology, 23(9):1105-1116 (2005).
Hountondji, C., et al., "Crucial Role of Conserved Lysine 277 in the Fidelity of tRNA Aminoacylation by *Escherichia coli* Valyl-tRNA Synthetase," Biochemistry, 41(50):14856-14865 (2002).
Hountondji, C., et al., "Valyl-tRNA Synthetase From *Escherichia coli* MALDI-MS Identification of the Binding Sites for L-Valine or for Noncognate Amino Acids Upon Qualitative Comparative Labeling With Reactive Amino-Acid Analogs," European Journal of Biochemistry, 267(15):4789-4798 (2000).
Hruby, V.J., et al., "Emerging Approaches in the Molecular Design of Receptor-Selective Peptide Ligands: Conformational, Topographical and Dynamic Considerations," The Biochemical Journal 268(2):249-262 (1990).
Huihui, K. M. M., et al., "Decarboxylative Cross-Electrophile Coupling of N-Hydroxyphthalimide Esters with Aryl Iodides," J Am Chem Soc., 138(15):5016-5019 (2016).
Ikeuchi, Y., et al., "Agmatine-conjugated cytidine in a tRNA anticodon is essential for AUA decoding in archaea," Nat Chem Biol., 6:277-282 (2010).
Ikeuchi, Y., et al., "Molecular Mechanism of Lysidine Synthesis that Determines tRNA Identity and Codon Recognition," Mol Cell, 19:235-246 (2005).

Itoh, Y., et al., "Crystallographic and Mutational Studies of Seryl-tRNA Synthetase From the Archaeon Pyrococcus Horikoshii," RNA Biology, 5(3):169-177 (2008).
Iwane, Y., et al., "Expanding the amino acid repertoire of ribosomal polypeptide synthesis via the artificial division of codon boxes," Nat Chem., 8:317-325 (2016).
Jaradat, D. M. M., "Thirteen decades of peptide synthesis: key developments in solid phase peptide synthesis and amide bond formation utilized in peptide ligation," Amino Acids, 50:39-68 (2018).
Jones, A. B., et al., "A Formal Synthesis of FK-506. Exploration of Some Alternatives to Macrolactamization," J Org Chem., 55:2786-2797 (1990).
Josephson, K., et al., "Ribosomal Synthesis of Unnatural Peptides," Journal of the American Chemical Society, 127(33):11727-11735 (2005).
Kato, et al., Yakubutsutaishagaku. 2nd edition, pp. 9-13 (2000).
Katoh, T., et al., "Ribosomal Synthesis of Backbone Macrocyclic Peptides," Chemical Communications, 47(36):9946-9958 (2011).
Kawakami, T. and Aimoto, S., "Sequential Peptide Ligation by Using a Controlled Cysteinyl Prolyl Ester (CPE) Autoactivating Unit," Tetrahedron Letters, 48(11):1903-1905, (2007).
Kawakami, T., et al., "Diverse Backbone-Cyclized Peptides via Codon Reprogramming," Nature Chemical Biology, 5(12):888-890 (2009).
Kawakami, T., et al., "In Vitro Selection of Multiple Libraries Created by Genetic Code Reprogramming to Discover Macrocyclic Peptides That Antagonize VEGFR2 Activity in Living Cells," ACS Chemical Biology 8(6):1205-1214 (2013).
Kiho, T., et al., "Total Synthesis of Pleofugin A, a Potent Inositol Phosphorylceramide Synthase Inhibitor," Org Lett., 20:4637-4640 (2018); Kiho, T., et al., "Correction to Total Synthesis of Pleofugin A, a Potent Inositol Phosphorylceramide Synthase Inhibitor," Org Lett., 20(20):6610 (2018).
Kleineweischede, R. and Hackenberger, C.P., "Chemoselective Peptide Cyclization by Traceless Staudinger Ligation," Angewandte Chemie (International ed. in English) 47(32):5984-5988 (2008).
Kobayashi, T., et al., "Recognition of Non-Alpha-Amino Substrates by pyrrolysyl-tRNA Synthetase," Journal of Molecular Biology, 385(5):1352-1360 (2009).
Kopina, B. J. and Lauhon, C. T., "Efficient Preparation of 2, 4-Diaminopyrimidine Nucleosides: Total Synthesis of Lysidine and Agmatidine," Org Lett., 14(16):4118-4121 (2012).
Kuhn, B., et al., "Intramolecular Hydrogen Bonding in Medicinal Chemistry," J Med Chem., 53:2601-2611 (2010).
Lajoie, M. J., et al., "Overcoming Challenges in Engineering the Genetic Code," J Mol Biol., 428:1004-1021 (2016).
Lassak, J., et al., "Stall No More at Polyproline Stretches With the Translation Elongation Factors EF-P and IF-5A," Molecular Microbiology, 99(2):219-235 (2016).
Laufer, B., et al., "The Impact of Amino Acid Side Chain Mutations in Conformational Design of Peptides and Proteins," Chemistry, 16(18):5385-5390 (2010).
Lee, K.W. and Briggs, J.M., "Molecular Modeling Study of the Editing Active Site of *Escherichia coli* leucyl-tRNA Synthetase: Two Amino Acid Binding Sites in the Editing Domain," Proteins, 54(4):693-704 (2004).
Lenzi, A., et al., "Synthesis of N-Boc-α-amino acids with nucleobase residues as building blocks for the preparation of chiral PNA (peptidic nucleic acids)," Tetrahedron Letters, 36(10):1713-1716 (1995).
Li, S., et al., "In Vitro Selection of mRNA Display Libraries Containing an Unnatural Amino Acid," Journal of the American Chemical Society, 124(34):9972-9973 (2002).
Li, X., et al., "Salicylaldehyde Ester-Induced Chemoselective Peptide Ligations: Enabling Generation of Natural Peptidic Linkages at the Serine/Threonine Sites," Org Lett., 12(8):1724-1727 (2010).
Li, H., et al., "Ni-Catalyzed Electrochemical Decarboxylative C—C Couplings in Batch and Continuous Flow," Org Lett., 20:1338-1341 (2018).
Liniger, M., et al., "Total Synthesis and Characterization of 7-Hypoquinuclidonium Tetrafluoroborate and 7-Hypoquinuclicone $BF_3$ Complex," J Am Chem Soc., 138:969-974 (2016).

(56) References Cited

OTHER PUBLICATIONS

Liu, D.R., et al., "Engineering a tRNA and aminoacyl-tRNA Synthetase for the Site-Specific Incorporation of Unnatural Amino Acids Into Proteins in Vivo," Proceedings of the National Academy of Sciences of the United States of America, 94(19):10092-10097 (1997).

Liu, T., et al., "Synthesis and Screening of a Cyclic Peptide Library: Discovery of Small-Molecule Ligands Against Human Prolactin Receptor," Bioorganic and Medicinal Chemistry, 17(3):1026-1033 (2009).

Liu, Z., et al., "N-Boc Deprotection and Isolation Method for Water-soluble Zwitterionic Compounds," The Journal of Organic Chemistry, 79(23):11792-11796 (2014).

Lodder, M., et al., "The N-Pentenoyl Protecting Group for Aminoacyl-tRNAs," Methods, 36(3):245-251 (2005).

Loos, P., et al., "Unified Azoline and Azole Syntheses by Optimized Aza-Wittig Chemistry," Eur J Org Chem. 2013(16):3290-3315 (2013).

Low, K.E., et al., "Rational Design of Calpain Inhibitors Based on Calpastatin Peptidomimetics," Journal of Medicinal Chemistry, 59(11):5403-5415 (2016).

Luo, D., et al., "Total Synthesis of the Potent Marine-Derived Elatase Inhibitor Lyngbyastatin 7 and in Vitro Biological Evaluation in Model Systems for Pulmonary Disease," J Org Chem., 81:532-544 (2016).

Lundquist, J.T. and Pelletier, J.C., "Improved Solid-Phase Peptide Synthesis Method Utilizing Alpha-Azide-Protected Amino Acids," Org Lett., 3(5):781-783 (2001).

Malhotra, R., et al., "Efficient Asymmetric Synthesis of N-Protected-B-Aryloxyamino Acids Via Regioselective Ring Opening of Serine Sulfamidate Carboxylic Acid," Organic & Biomolecular Chemistry, 12(33):6507-6515 (2014).

Manfredini, S., et al., "Design and synthesis of phosphonoacetic acid (PPA) ester and amide bioisosters of ribofuranosylnucleoside diphosphates as potential ribonucleotide reductase inhibitors and evaluation of their enzyme inhibitory, cytostatic and antiviral activity," Antivir Chem Chemother., 14:183-194 (2003).

Mangold, S.L., et al., "Z-Selective Olefin Metathesis on Peptides: Investigation of Side-Chain Influence, Preorganization, and Guidelines in Substrate Selection," Journal of the American Chemical Society, 136(35):12469-12478 (2014).

Mas-Moruno, C., et al., "Cilengitide: The First Anti-Angiogenic Small Molecule Drug Candidate Design, Synthesis, and Clinical Evaluation," Anti-Cancer Agents in Medicinal Chemistry, 10(10):753-768 (2010).

Meinnel, T., et al., "Methionine as Translation Start Signal: A Review of the Enzymes of the Pathway in *Escherichia coli*," Biochimie 75(12):1061-1075 (1993).

Mermershtain, I., et al., "Idiosyncrasy and Identity in the Prokaryotic Phe-system: Crystal Structure of *E. coli* phenylalanyl-tRNA Synthetase Complexed With Phenylalanine and AMP," Protein Science 20(1):160-167 (2011).

Merryman, C. and Green, R., "Transformation of Aminoacyl tRNAs for the in Vitro Selection of "Drug-Like" Molecules," Chemistry & Biology, 11(4):575-582 (2004).

Millward, S.W., et al., "Design of Cyclic Peptides That Bind Protein Surfaces With Antibody-Like Affinity," ACS Chemical Biology 2(9):625-634 (2007).

Miyake, A., et al., "Design and Synthesis of N-[N-(S)-1-Ethoxycarbonyl-3-pheylpropyl]-L-alanyl]-N-(indan-2-yl)glycine (CV-3317), a New, Potent Angiotensin Converting Enzyme Inhibitor," Chem Pharm Bull., 34(7):2852-2858 (1986).

Montalbetti, C.A.G.N. and Falque, V., "Amide Bond Formation and Peptide Coupling," Tetrahedron, 61(46):10827-10852 (2005).

Morieux, P., et al., "The Structure-Activity Relationship of the 3-Oxy Site in the Anticonvulsant (R)-N-Benzyl 2-Acetamido-3-Methoxypropionamide," Journal of Medicinal Chemistry, 53(15):5716-5726 (2010).

Muramatsu, T., et al., "A Novel Lysine-Substituted Nucleoside in The First Position of the Anticodon of Minor Isoleucine tRNA from *Escherichia coli*," The Journal of Biological Chemistry, 263(19):9261-9267 (1988).

Murashige, R., et al., "Asymmetric and efficient synthesis of homopheylalanine derivatives via Friedel-Crafts reaction with trifluoromethanesulfonic acid," Tetrahedron Letters, 49(46):6566-6568 (2008).

Navo, C.D., et al., "Oxygen by Carbon Replacement at the Glycosidic Linkage Modulates the Sugar Conformation in Tn Antigen Mimics," ACS Omega, 3(12);18142-18152 (2018).

Niida, A., et al., "Investigation of the Structural Requirements of K-Ras(G12D) Selective Inhibitory Peptide KRpep-2d Using Alanine Scans and Cysteine Bridging," Bioorganic & Medicinal Chemistry Letters, 27(12):2757-2761 (2017).

Ohta, A., et al., "Synthesis of Polyester by Means of Genetic Code Reprogramming," Chemistry & Biology, 14(12):1315-1322 (2007).

Ohtsuki, T., et al., "Phototriggered Protein Syntheses by Using (7-diethylaminocoumarin-4-yl)Methoxycarbonyl-Caged Aminoacyl tRNAs," Nature Communications 7:12501 (2016).

Ohwada, T., et al., "On the Planarity of Amide Nitrogen. Intrinisic Pyramidal Nitrogen of N-Acyl-7-Azabicyclo[2.2.1]heptanes," Tetrahedron Lett., 39:865-868 (1998).

Orain, D., et al., "Protecting Groups in Solid-Phase Organic Synthesis," J Comb Chem., 4(1):1-16 (2002).

Osawa, T., et al., "Structural basis of tRNA agmatinylation essential for AUA codon decoding," Nat Struct Mol Biol., 18(11):1275-1280 (2011).

Ostrem, J. M. L. and Shokat, K. M., "Direct small-molecule inhibitors of KRAS: from structural insights to mechanism-based design," Nat Rev Drug Discov., 15:771-785 (2016).

Ovadia, O., et al., "Improvement of Drug-Like Properties of Peptides: The Somatostatin Paradigm," Expert Opinion on Drug Discovery, 5(7):655-671 (2010).

Parthasarathy, R., et al., "Sortase A as a Novel Molecular "Stapler" for Sequence-Specific Protein Conjugation," Bioconjugate Chemistry, 18(2):469-476 (2007).

Peacock, J.R., et al., "Amino Acid-Dependent Stability of the Acyl Linkage in aminoacyl-tRNA," RNA, 20(6):758-764 (2014).

Perona, J.J. and Hadd, A., "Structural Diversity and Protein Engineering of the aminoacyl-tRNA Synthetases," Biochemistry, 51(44):8705-8729 (2012).

Peschke, B., et al., "New highly potent dipeptidic growth hormone secretagogues with low molecular weight," Eur J Med Chem., 35:599-618 (2000).

Piszkiewicz, D., et al., "Anomalous Cleavage of Aspartyl-Proline Peptide Bonds During Amino Acid Sequence Determinations," Biochemical and Biophysical Research Communications, 40(5):1173-1178 (1970).

Räder, A. F. B., et al., "Orally Active Peptides: Is There a Magic Bullet?," Angew Chem Int Ed., 57:14414-14438 (2018).

Rafi, S. B., et al., "Predicting and Improving the Membrane Permeability of Peptidic Small Molecules," J Med Chem., 55:3163-3169 (2012).

Reddy, P.R., et al., "Synthesis of Small Cyclic Peptides via Intramolecular Heck Reactions," Tetrahedron Letters, 44(2):353-356 (2003).

Rezai, T., et al., "Testing the Conformational Hypothesis of Passive Membrane Permeability Using Synthetic Cyclic Peptide Diastereomers," Journal of the American Chemical Society, 128(8):2510-2511 (2006).

Sakamoto, K., et al., "K-Ras(G12D)-selective inhibitory peptides generated by random peptide T7 phage display technology," Biochem Biophys Res Commun., 484:605-611 (2017).

Salowe, S.P., et al., "The Catalytic Flexibility of Trnaile-Lysidine Synthetase can Generate Alternative tRNA Substrates for Isoleucyl-tRNA Synthetase," The Journal of Biological Chemistry, 284(15):9656-9662 (2009).

Samatar, A. A. and Poulikakos, P. I., "Targeting RAS-ERK signaling in cancer: promises and challenges," Nat Rev Drug Discov., 13:928-942 (2014).

(56) References Cited

OTHER PUBLICATIONS

Sang-Aroon, W. and Ruangpornvisuti, V., "Theoretical study on isomerization and peptide bond cleavage at aspartic residue," J Mol Model, 19:3627-3636 (2013).
Sankaranarayanan, R., et al., "The Structure of threonyl-tRNA synthetase-tRNA(Thr) Complex Enlightens Its Repressor Activity and Reveals an Essential Zinc Ion in the Active Site," Cell, 97(3):371-381 (1999).
Satyanarayanajois, S.D. and Hill, R.A., "Medicinal Chemistry for 2020," Future Medicinal Chemistry, 3(14):1765-1786 (2011).
Schlippe, Y.V.G., et al., "In Vitro Selection of Highly Modified Cyclic Peptides That Act as Tight Binding Inhibitors," Journal of the American Chemical Society 134(25):10469-10477 (2012).
Sever, S., et al., "*Escherichia coli* tryptophanyl-tRNA Synthetase Mutants Selected for Tryptophan Auxotrophy Implicate the Dimer Interface in Optimizing Amino Acid Binding," Biochemistry, 35(1):32-40 (1996).
Shimizu, Y., et al., "Cell-Free Translation Reconstituted With Purified Components," Nature Biotechnology, 19(8):751-755 (2001).
Shukla, G.S. and Krag, D.N., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, 13(1):75-87 (2010).
Sogabe, S., et al., "Crystal Structure of a Human K-Ras G12D Mutant in Complex with GDP and the Cyclic Inhibitory Peptide KRpep-2D," ACS Med Chem Lett., 8:732-736 (2017).
Starosta, A.L., et al., "A Conserved Proline Triplet in Val-tRNA Synthetase and the Origin of Elongation Factor P," Cell Reports, 9(2):476-483 (2014).
Stetsenko, D. A., et al., "Removal of Acid-Labile Protecting or Anchoring Groups in the Presence of Polyfluorinated Alcohol: Application to Solid-Phase Peptide Synthesis," Russian Journal of Bioorganic Chemistry, 42(2):143-152 (2016).
Struck, A.-W., et al., "An Enzyme Cascade for Selective Modification of Tyrosine Residues in Structurally Diverse Peptides and Proteins," J Am Chem Soc., 138:3038-3045 (2016).
Suenaga, K., et al., "Aurilide, a cytotoxic depsipeptide from the sea hare *Dolabella auricularia*: isolation, structure determination, synthesis, and biological activity," Tetrahedron, 60:8509-8527 (2004).
Suenaga, K., et al., "Synthesis and cytotoxicity of aurilide analogs," Bioorg Med Chem Lett., 18:3902-3905 (2008).
Suzuki, T. and Miyauchi, K., "Discovery and characterization of tRNA$^{Ile}$ lysidine synthetase (TilS)," FEBS Lett., 584:272-277 (2010).
Suzuki, "The Genetic Code Deciphering Mechanism in Archaea," Kagaku to Seibutsu, 50(1):36-43 (2012).
Tan, Z., et al., "Amino Acid Backbone Specificity of the *Escherichia coli* Translation Machinery," Journal of the American Chemical Society, 126(40):12752-12753 (2004).
Terasaka, et al., "Construction of Nonstandard Peptide Library by Genetic Code Reprogramming and Bioactive Peptide Discovery," Experimental Medicine, 29(7):1063-1070 (2011).
Terasaka, N., et al., "Recent Developments of Engineered Translational Machineries for the Incorporation of Non-Canonical Amino Acids Into Polypeptides," International Journal of Molecular Sciences, 16(3):6513-6531 (2015).
Toriyama, F., et al., "Redox-Active Esters in Fe-Catalyzed C—C Coupling," J Am Chem Soc., 138(35):11132-11135 (2016).
Tsukiji, S. and Nagamune, T., "Sortase-mediated Ligation: A Gift From Gram-positive Bacteria to Protein Engineering," Chembiochem., 10(5):787-798 (2009).
Vaisar, T. and Urban, J., "Gas-phase Fragmentation of Protonated Mono-N-methylated Peptides. Analogy with Solution-phase Acid-catalyzed Hydrolysis," J Mass Spectrometry, 33:505-524 (1998).
Van Der Auwera, C. and Anteunis, M. J. O., "Easy cleavage of C'-terminal iminoacids from peptide acids through acidic hydrolysis," Int J Peptide Protein Res., 31:186-191 (1988).
Wang, T. and Danishefsky, S. J., "Revisiting Oxytocin through the Medium of Isonitriles," J Am Chem Soc., 134:13244-13247 (2012).

Wang, S., et al., "Iridium/f-Amphox-Catalyzed Asymmetric Hydrogenation of Styrylglyoxylamides," Synlett., 29(16):2203-2207 (2018).
Watanabe, E., et al., "A Practical Method for Continuous Production of sp3-rich Compounds from (Hetero)Aryl Halides and Redox-Active Esters," Chem Eur J., 26:186-191 (2020).
Weber, F., et al., "A Potato Mitochondrial Isoleucine tRNA is Coded for by a Mitochondrial Gene Possessing a Methionine Anticodon," Nucleic Acids Research, 18(17):5027-5030 (1990).
Wells, J.A. and McClendon, C.L., "Reaching for High-Hanging Fruit in Drug Discovery at Protein-Protein Interfaces," Nature, 450(7172):1001-1009 (2007).
Wermuth, C.G., "The Practice of Medicinal Chemistry," 2nd Edition, vol. 1, P87 (2003), with English translation, Wermuth, C. G., "The Practice of Medicinal Chemistry," 2nd Edition, Academic Press, pp. 52-53 (2003).
White, C.J. and Yudin, A.K., "Contemporary Strategies for Peptide Macrocyclization," Nature Chemistry, 3(7):509-524 (2011).
Wu, J. and Lebrilla, C. B., "Intrinsic Basicity of Oligomeric Peptides that Contain Glycine, Alanine, and Valine—The Effects of the Alkyl Side Chain on Proton Transfer Reactions," J Am Soc Mass Spectrom., 6:91-101 (1995).
Wu, N., et al., "A Genetically Encoded Photocaged Amino Acid," Journal of the American Chemical Society, 126(44):14306-14307 (2004).
Yajima, et al., "New Strategy for the Chemical Synthesis of Proteins," Tetrahedron, 44(3):805-819 (1988).
Yamanoi, K. and Ohfune, Y., "Synthesis of Trans—and Cis-α-(Carboxycyclopropyl)Glycines. Novel Neuroinhibitory Amino Acids as L-Glutamate Analogue," Tetrahedron Lett., 29(10):1181-1184 (1988).
Yanagisawa, T., et al., "Multistep Engineering of Pyrrolysyl-tRNA Synthetase to Genetically Encode N(epsilon)-(o-azidobenzyloxycarbonyl) Lysine for Site-Specific Protein Modification," Chemistry & Biology, 15(11):1187-1197 (2008).
Yang, Side Reactions in Peptide Synthesis, pp. 1-31 (2015).
Yao, G., et al., "Efficient Synthesis and Stereochemical Revision of Coibamide A," J Am Chem Soc., 137:13488-13491 (2015).
Zhai, Y. and Martinis, S.A., "Two Conserved Threonines Collaborate in the *Escherichia coli* Leucyl-tRNA Synthetase Amino Acid Editing Mechanism," Biochemistry, 44(47):15437-15443 (2005).
Zhang, B., et al., "Specificity of Translation for N-Alkyl Amino Acids," Journal of the American Chemical Society 129(37):11316-11317 (2007).
Zhang, K., et al., "Ab Initio Studies of Neutral and Protonated Triglycines: Comparison of Calculated and Experimental Gas-Phase Basicity," J Am Chem Soc., 116:11512-11521 (1994).
Zhang, A. J., et al., "A Method for Removal of N-BOC Protecting Groups from Substrates on TFA-sensitive Resins," Tetrahedron Lett., 39:7439-7442 (1998).
U.S. Appl. No. 07/331,292, filed Mar. 30, 1989, Yajima, et al.
U.S. Appl. No. 10/345,664, filed Jan. 16, 2003, Olejnik, et al.
U.S. Appl. No. 11/682,272, filed Mar. 5, 2007, Wang, et al.
U.S. Appl. No. 13/505,625, filed Oct. 22, 2012, Strom, et al.
U.S. Appl. No. 13/816,911, filed Feb. 13, 2013, Suga, et al.
U.S. Appl. No. 14/125,906, filed Mar. 10, 2014, Gao, et al.
U.S. Appl. No. 14/428,804, filed Mar. 17, 2015, Van, et al.
U.S. Appl. No. 14/889,868, filed Mar. 7, 2016, Murakami, et al.
U.S. Appl. No. 16/619,014, filed Dec. 3, 2019, Muraoka, et al.
U.S. Appl. No. 17/024,944, filed Sep. 18, 2020, Ohta, et al., related application.
U.S. Appl. No. 17/291,099, 371(c) date May 4, 2021, Ishizawa, related application.
U.S. Appl. No. 17/297,231, 371(c) date May 26, 2021, Iwasaki, et al., related application.
U.S. Appl. No. 17/312,296, 371(c) date Jun. 9, 2021, Muraoka, et al., related application.
U.S. Appl. No. 17/417,822, 371(c) date Jun. 24, 2021, Shinohara, et al., related application.
Albericio, F., et al., "Fmoc Methodology: Cleavage from the Resin and Final Deprotection," Amino Acids, Peptides and Proteins in Organic Chemistry, 3:349-369 (2011).

(56) References Cited

OTHER PUBLICATIONS

Beck, J. G., et al., "Intestinal Permeability of Cyclic Peptides: Common Key Backbone Motifs Identified," J Am Chem Soc., 134:12125-12133 (2012).
Behrendt, R., et al., "Advances in Fmoc solid-phase peptide synthesis," J Pept Sci., 22:4-27 (2016).
Bock, J. E., et al., "Getting in Shape: Controlling Peptide Bioactivity and Bioavailability Using Conformational Constraints," ACS Chem Biol., 8:488-499 (2013).
Carpino, L. A., et al., "Dramatically enhanced N→O acyl migration during the trifluoroacetic acid-based deprotection step in solid phase peptide synthesis," Tetrahedron Letters, 46:1361-1364 (2005).
Chatterjee, J., et al., "N-Methylation of Peptides: A New Perspective in Medicinal Chemistry," Acc Chem Res., 41(10):1331-1342 (2008).
Doi, Y., et al., "Elongation Factor Tu Mutants Expand Amino Acid Tolerance of Protein Biosynthesis System," J Am Chem Soc., 129:14458-14462 (2007).
Eberhard, H. and Seitz, O., "N→O Acyl shift in Fmoc-based synthesis of phosphopeptides," Org Biomol Chem., 6:1349-1355 (2008).
Fang, W.-J., et al., "Deletion of Ac-NMePhe From [NMePhe]arodyn Under Acidic Conditions, Part 1: Effects of Cleavage Conditions and N-Terminal Functionality," Peptide Science, 96(1):97-102 (2011).
Fujino, T., et al., "Reevaluation of the D-Amino Acid Compatibility with the Elongation Event in Translation," J Am Chem Soc., 135:1830-1837 (2013).
Fujino, T., et al., "Ribosomal Synthesis of Peptides with Multiple β-Amino Acids," J Am Chem Soc., 138:1962-1969 (2016).
Gracia, S. R., et al., "Synthesis of chemically modified bioactive peptides: recent advances, challenges and developments for medicinal chemistry," Future Med Chem., 1(7):1289-1310 (2009).
Hartman, M. C. T., et al., "An Expanded Set of Amino Acid Analogs for the Ribosomal Translation of Unnatural Peptides," PLoS One, 2(10):e972 (2007), 15 pages.
Hecht, S. M., et al., "'Chemical Aminoacylation' of tRNA's," J Biol Chem., 253(13):4517-4520 (1978).
International Search Report in International Patent Application No. PCT/JP2018/046021 dated Mar. 12, 2019, 2 pages.
Josephson, K., et al., "mRNA display: from basic principles to macrocycle drug discovery," Drug Discovery Today, 19(4):388-399 (2014).
Kato, et al., Yakubutsutaishagaku, 3rd edition, 43-46 (2010).
Kawakami, T., et al., "Messenger RNA-Programmed Incorporation of Multiple N-Methyl-Amino Acids into Linear and Cyclic Peptides," Chem Biol., 15:32-42 (2008).
Kawakami, T., et al., "Incorporation of electrically charged N-alkyl amino acids into ribosomally synthesized peptides via post-translational conversion," Chem Sci., 5:887-893 (2014).
Kawakami, T., et al., "Ribosomal Synthesis of Polypeptides and Peptoid-Peptide Hybrids," J Am Chem Soc., 130:16861-16863 (2008).
Maini, R., et al., "Protein Synthesis with Ribosomes Selected for the Incorporation of β-Amino Acids," Biochem., 54:3694-3706 (2015).
Maini, R., et al., "Ribosome-mediated synthesis of natural product-like peptides via cell-free translation," Curr Opin Chem Biol., 34:44-52 (2016).
Marcucci, E., et al., "Solid-Phase Synthesis of NMe-IB-01212, a Highly N-Methylated Cyclic Peptide," Org Lett., 14(2):612-615 (2012).
Millward, S. W., et al., "A General Route for Post-Translational Cyclization of mRNA Displays Libraries," J Am Chem Soc., 127:14142-14143 (2005).
Rodríguez, H., et al., "A convenient microwave-enhanced solid-phase synthesis of short chain N-methyl-rich peptides," J Pept Sci., 16:136-140 (2010).
Roodbeen, R., et al., "Microwave Heating in the Solid-Phase Synthesis of N-Methylated Peptides: When Is Room Temperature Better?" Eur J Org Chem., 2012:7106-7111 (2012).
Subtelny, A. O., et al., "Ribosomal Synthesis of N-Methyl Peptides," J Am Chem Soc., 130:6131-6136 (2008).
Subtelny, A. O., et al., "Optimal Codon Choice can Improve the Efficiency and Fidelity of N-Methyl Amino Acid Incorporation into Peptides by In Vitro Translation," Angew Chem Int Ed Engl., 50(14):3164-3167 (2011).
Teixidó, M., et al., "Solid-phase synthesis and characterization of N-methyl-rich peptides," J Peptide Res., 65:153-166 (2005).
Urban, J., et al., "Lability of N-alkylated peptides towards TFA cleavage," Int J Peptide Protein Res., 47:182-189 (1996).
Wang, J., et al., "Kinetics of Ribosome-Catalyzed Polymerization Using Artificial Aminoacyl-tRNA Substrates Clarifies Inefficiencies and Improvements," ACS Chem Biol., 10:2187-2192 (2015).
Wenschuh, H., et al., "Stepwise Automated Solid Phase Synthesis of Naturally Occurring Peptaibols Using FMOC Amino Acid Fluorides," J Org Chem., 60:405-410 (1995).
White, T. R., et al., "On-resin N-methylation of cyclic peptides for discovery of orally bioavailable scaffolds," Nat Chem Biol., 7:810-817 (2011).
Yamagishi, Y., et al., "Natural Product-Like Macrocyclic N-Methyl-Peptide Inhibitors against a Ubiquitin Ligase Uncovered from a Ribosome-Expressed De Novo Library," Chem Biol., 18:1562-1570 (2011).
Yang, Y., "Side Reactions in Peptide Synthesis," 246 (2016).
U.S. Appl. No. 14/368,564, 371(c) date Jun. 25, 2014, Kariyuki, S., et al., related application.
U.S. Appl. No. 15/166,550, filed May 27, 2016, Kariyuki, S., et al., related application.
U.S. Appl. No. 15/557,532, 371(c) date Jan. 10, 2018, Ohta, A., et al., related application.
U.S. Appl. No. 16/081,522, 371(c) date Jul. 8, 2019, Nakano, K., et al., related application.
U.S. Appl. No. 16/479,736, 371(c) date Jul. 22, 2019, Tanaka, S., et al., related application.
U.S. Appl. No. 16/619,388, 371(c) date Dec. 4, 2019, Nomura, K., et al., related application.
U.S. Appl. No. 17/011,815, filed Sep. 3, 2020, Kariyuki, S., et al., related application.
U.S. Appl. No. 14/368,564, 371(c) date Jun. 25, 2014, Kariyuki, S., et al.
U.S. Appl. No. 15/166,550, filed May 27, 2016, Kariyuki, S., et al.
U.S. Appl. No. 15/557,532, 371(c) date Jan. 10, 2018, Ohta, A., et al.
U.S. Appl. No. 16/081,522, 371(c) date Jul. 8, 2019, Nakano, K., et al.
U.S. Appl. No. 16/479,736, 371(c) date Jul. 22, 2019, Tanaka, S., et al.
U.S. Appl. No. 16/619,388, 371(c) date Dec. 4, 2019, Nomura, K., et al.
U.S. Appl. No. 17/011,815, filed Sep. 3, 2020, Kariyuki, S., et al.
Isidro-Llobet, A., et al., "Amino Acid-Protecting Groups," Chem Rev., 109:2455-2504 (2009).
Lejeune, V., et al., "Towards a selective Boc deprotection on acid cleavable Wang resin," Tetrahedron Lettters, 44:4757-4759 (2003).
Tam, J. P., et al., "Cyclohexyl Ester as a New Protecting Group for Aspartyl Peptides to Minimize Aspartimide Formation in Acidic and Basic Treatments," Tetrahedron Letters, 42:4033-4036 (1979).
Tsuda, et al., Amino Acids, Peptides and Proteins in Organic Chemistry, 3:201-406, 495-517, 549-569 (2011).
U.S. Appl. No. 17/437,535, filed Sep. 9, 2021, Wadamoto, related application.

* cited by examiner

METHOD FOR PRODUCING PEPTIDE, AND METHOD FOR PROCESSING BASES

CROSS-REFERENCE TO RELATED APPLICATIONS

This application is a U.S. National Phase of PCT Application No. PCT/JP2018/046021, filed Dec. 14, 2018, which claims the benefit of Japanese Patent Application No. 2017-240180, filed Dec. 15, 2017, each of which is incorporated herein by reference in its entirety.

TECHNICAL FIELD

The present disclosure relates to methods of producing peptides, methods of treating bases for use in the methods of producing peptides, inactivating agents for bases for use in the same, and such.

BACKGROUND ART

Methods such as solid-phase synthesis and liquid-phase synthesis have been reported as methods of chemically synthesizing peptides. Typically, in any of these methods, a peptide chain is elongated by coupling the carboxy group of a newly added amino acid to the amino group of the growing peptide chain to form an amide bond. In this case, it is known that the peptide chain can be elongated while suppressing side reactions by protecting, with protecting groups, reactive functional groups other than the functional group to be used for the amide bond. More specifically, the amino group of a newly added amino acid is protected with a protecting group, and after the amino acid is coupled to the peptide chain, the protecting group is removed (deprotection). The amino group thus exposed is coupled to the carboxy group of a new amino acid subsequently added. Methods that repeat this procedure to elongate a peptide chain is being utilized.

Specific examples of typical peptide synthesis methods include a known method that elongates a peptide chain by repeating the steps of: coupling the carboxy group of an amino acid protected with an Fmoc group (an Fmoc amino acid) at the N terminus to the amino group of the growing peptide chain via an amide bond; and then removing the Fmoc group using a basic deprotecting agent such as piperidine or DBU.

However, it has been reported that in this method, when piperidine, a deprotecting agent, remains in the peptide chain elongation step, such piperidine may cause removal of the Fmoc group of the Fmoc amino acid used for the subsequent elongation, resulting in redundant peptide elongation due to double coupling of the same amino acid and such (Non-Patent Literature 1). As a method for suppressing such redundant elongation, a method of repeating washing until the remaining piperidine cannot be detected has been reported (Non-Patent Literature 1).

CITATION LIST

Non-Patent Literature

Non-Patent Literature 1: Yi Yang, Side Reactions in Peptide synthesis, 2016, p. 246

SUMMARY OF INVENTION

Technical Problem

As described above, in methods of chemically synthesizing peptides, washing is typically repeated to remove remaining reagents such as a deprotecting agent every time an amino acid is coupled to the peptide chain. However, frequent washing causes problems such as prolongation of production time and equipment utilization time, cost increases associated therewith, and requirement of a large amount of a solvent used for washing. Furthermore, insufficient washing causes a problem such that a purity of a target peptide may be reduced by production of by-products. In particular, in peptide synthesis methods in which an amino acid elongation step is repeated, even if only a small amount of by-products is produced in a single amino acid elongation step, such by-products may be accumulated by repeating this step, thereby resulting in considerable reduction of the purity of the target peptide.

The present invention was achieved in view of the above circumstances. In a non-limiting aspect, an objective of the present invention is to provide novel methods of treating deprotecting agents. In a non-limiting aspect, an objective of the present invention is to provide peptide production methods that can suppress redundant peptide elongation caused by remaining deprotecting agents. In a non-limiting aspect, an objective of the present invention is to provide methods of treating bases in the peptide production methods. In a non-limiting aspect, an objective of the present invention is to provide base-inactivating agents used in the peptide production methods.

Solution to Problem

The present inventors have found a method of suppressing redundant peptide elongation by inactivating a deprotecting agent, instead of by removing a remaining deprotecting agent by washing. When the deprotecting agent is a base, neutralization with an acid can be selected as a method of inactivating the base. However, if an acid is simply added, not only is the deprotecting agent neutralized, but the N-terminus of the growing peptide chain may be protonated resulting in reduced elongation reactivity. Further, when a linker that is highly sensitive to acids (such as 2-CTC) is used for the linkage site between a solid-phase support and a peptide, the growing peptide chain may be cleaved from the solid-phase support by an acid. As reported, such cleavage from the solid-phase support in the course of peptide elongation can be observed even at an acidity of oxyma (ethyl cyano(hydroxyimino)acetate) (pKa=4.60) widely used for common peptide elongation (P. Cherkupally, et al., K-Oxyma: a Strong Acylation-Promoting, 2-CTC Resin-Friendly Coupling Additive, Eur. J. Org. Chem., 2013, 6372-6378). In recent years, peptides containing N-methyl-amino acids have attracted attention (WO 2013/100132). It has been reported, however, that acid treatment in the course of synthesis of peptides containing N-methylamino acids may cause such side reactions as peptide chain cleavage (M. Teixido, et al. Solid-phase synthesis and characterization of N-methyl-rich peptides. J. Peptide Res., 2005, 65, 153; J. Urban, et al., Lability of N-alkylated peptides towards TFA cleavage. Int. J. Pept. Prot. Res., 1996, 47, 182). There is a need to avoid undesirable side reactions due to the above-described action of acids.

The present inventors have thus found a method of inactivating a deprotecting agent by a salt formed of an acid and a base that is different in type from the deprotecting agent, thereby completing the present invention.

In a non-limiting specific embodiment, the present invention includes the following.

[1] A method of producing a peptide, the method comprising the steps of:

(a) allowing a base X, an amino group-containing compound, and a salt formed of a base Y and an acid Z to coexist; and (b) after the step (a), allowing the amino group-containing compound and an amino acid or peptide having an amino group protected by a protecting group P to coexist to thereby elongate a peptide chain;

wherein a conjugate acid of the base Y has a pKa smaller than that of a conjugate acid of the base X.

[2] A method of treating a base X in production of a peptide, the method comprising the step (a) according to [1], wherein a conjugate acid of the base Y has a pKa smaller than that of a conjugate acid of the base X.

[3] The method according to [2], further comprising the step (b) according to [1].

[4] A method of producing a peptide, the method comprising the treatment method according to [2] or [3].

[5] The method according to any one of [1] to [4], wherein the step (a) is performed by mixing the base X, the amino group-containing compound, and the salt formed of the base Y and the acid Z.

[6] The method according to any one of [1] to [5], wherein the step (a) is performed by mixing a mixture comprising the base X and the amino group-containing compound with the salt formed of the base Y and the acid Z.

[7] The method according to any one of [1] to [6], wherein the step (a) is a step for inactivating the base X.

[8] The method according to any one of [1] and [3] to [7], wherein the step (b) is performed by mixing a mixture comprising the amino group-containing compound with the amino acid or peptide having an amino group protected by the protecting group P.

[9] The method according to any one of [1] to [8], further comprising, prior to the step
(a), the step of:
(a') removing with the base X a protecting group Q of the amino group-containing compound protected by the protecting group Q.

[10] The method according to any one of [1] to [9], wherein the base X is a deprotecting agent for the amino group protected by the protecting group Q.

[11] The method according to any one of [1] to [10], wherein the protecting group P in [1] or the protecting groups P and Q in [9] or [10] are a protecting group removable with a base.

[12] The method according to [11], wherein the protecting group removable with a base is a protecting group removable with the base X.

[13] The method according to [12], wherein the protecting group removable with the base X is a protecting group having an Fmoc backbone.

[14] The method according to [13], wherein the protecting group having an Fmoc backbone is an Fmoc group.

[15] The method according to any one of [9] to [14], wherein the protecting group Q is a protecting group of the same type as the protecting group P.

[16] The method according to any one of [1] to [15], wherein the base X is an organic base.

[17] The method according to any one of [1] to [16], wherein the base X is at least one type of a base selected from the group consisting of an amine, a base having an amidine backbone, and a base having a guanidine backbone.

[18] The method according to any one of [1] to [17], wherein the base X is a base having an amidine backbone.

[19] The method according to any one of [1] to [18], wherein the base X is at least one type of a base selected from the group consisting of DBU and piperidine.

[20] The method according to any one of [1] to [19], wherein the base X is DBU.

[21] The method according to any one of [1] to [20], wherein the amino group-containing compound is (i) an amino group-containing compound attached to a solid-phase support or (ii) an amino group-containing compound having a carboxy group protected by a protecting group.

[22] The method according to [21], wherein the solid-phase support according to (i) is a solid-phase support that cannot be removed with a base, or wherein the protecting group according to (ii) is a protecting group that cannot be removed with a base.

[23] The method according to any one of [1] to [22], wherein the amino group-containing compound is an amino group-containing compound attached to a solid-phase support.

[24] The method according to any one of [1] to [23], wherein the amino group-containing compound is an amino group-containing compound having at least one free primary amino group or free secondary amino group.

[25] The method according to any one of [21] to [24], wherein the solid-phase support is a solid-phase support containing a linker that cannot be cleaved by a base.

[26] The method according to any one of [21] to [25], wherein the solid-phase support is an acid-sensitive solid-phase support.

[27] The method according to [26], wherein the acid-sensitive solid-phase support is an acid-sensitive solid-phase support containing a trityl group.

[28] The method according to any one of [1] to [27], wherein the amino group-containing compound is an amino acid or peptide having at least one free primary amino group or free secondary amino group.

[29] The method according to any one of [1] to [28], wherein the amino group-containing compound has one free secondary amino group.

[30] The method according to [29], wherein the free secondary amino group is a free N-alkyl (C1-6) amino group.

[31] The method according to [29] or [30], wherein the free secondary amino group is a free N-methylamino group.

[32] The method according to any one of [1] and [4] to [31], wherein the peptide is produced by solid-phase synthesis.

[33] The method according to any one of [1] to [32], wherein the conjugate acid of the base Y has a pKa of 5.0 or more.

[34] The method according to any one of [1] to [33], wherein the conjugate acid of the base Y has a pKa of 9.0 or more.

[35] The method according to any one of [1] to [34], wherein the conjugate acid of the base Y has a pKa larger than that of a conjugate acid of the N-terminal amino group of the amino group-containing compound.

[36] The method according to any one of [1] to [35], wherein the conjugate acid of the base Y has a pKa of 15.0 or less.

[37] The method according to any one of [1] to [36], wherein the conjugate acid of the base Y has a pKa of 11.5 or less.

[38] The method according to any one of [1] to [37], wherein the base Y is an organic base.

[39] The method according to any one of [1] to [38], wherein the base Y is an amine or pyridine series.

[40] The method according to any one of [1] to [39], wherein the base Y is at least one base selected from the group consisting of triethylamine and N,N-diisopropylethylamine.

[41] The method according to any one of [1] to [40], wherein the acid Z is an acid having a pKa of 5.0 or less.

[42] The method according to any one of [1] to [41], wherein the acid Z is an acid having a pKa of −10.0 or more.

[43] The method according to any one of [1] to [42], wherein the conjugate acid of the base Y has a pKa larger than that of the acid Z.

[44] The method according to any one of [1] and [3] to [43], wherein the amino acid or peptide having an amino group protected by the protecting group P is an amino acid or peptide having at least one carboxy group that is free or converted to an active ester.

[45] The method according to any one of [1] and [3] to [44], wherein the amino acid or peptide having an amino group protected by the protecting group P is an amino acid or peptide which has one carboxy group that is free or converted to an active ester and in which the other reactive functional groups are protected by protecting groups.

[46] The method according to any one of [1] and [4] to [45], wherein the steps (a') to (b) are repeated twice or more.

[47] The method according to any one of [1] and [3] to [46], wherein the method does not comprise a washing step or comprises one to five washing steps between the steps (a) and (b).

[48] The method according to any one of [1] and [3] to [47], wherein the method does not comprise a washing step or comprises one to five washing steps in total between the steps (a) and (b) and between the steps (a') and (a).

[49] The method according to any one of [1] and [3] to [48], wherein the step (b) is performed in the presence of a condensing agent.

[50] The method according to any one of [1] and [3] to [49], wherein the peptide chain is elongated via amide bonds in the step (b).

[51] The method according to any one of [1] and [3] to [50], further comprising, after the step (b), the step of:
(c) cleaving the peptide from the solid-phase support.

[52] The method according to any one of [1] and [3] to [51], further comprising, after the step (b), the step of:
(c') removing the protecting groups of the peptide.

[53] The method according to any one of [1] and [4] to [52], wherein the method of producing a peptide is a method of producing a peptide containing at least one N-substituted amino acid.

[54] The method according to [53], wherein the N-substituted amino acid is an N-alkylamino acid.

[55] The method according to [54], wherein the N-alkylamino acid is an N-alkyl (C1-3) amino acid.

[56] The method according to [55], wherein the N-alkyl (C1-3) amino acid is N-methylamino acid.

[57] A peptide produced by the method according to any one of [1] and [4] to [56].

[58] An inactivating agent for a base X for use in the method according to any one of [1] to [56], wherein the inactivating agent comprises a salt formed of the base Y and the acid Z.

Effects of the Invention

According to some embodiments of the present invention, redundant peptide elongation can be suppressed. In some embodiments, washing frequency and an amount of washing solution can also be reduced. In some embodiments, high purity peptides can also be produced with only a small amount of by-products.

DESCRIPTION OF EMBODIMENTS

Abbreviations used herein are summarized below.

TABLE 1

| Abbreviation | Name |
|---|---|
| Boc | t-Butoxycarbonyl |
| BOP | 1H-Benzotriazol-1-yloxy-tris(dimethylamino)phosphonium hexafluorophosphate |
| 2-CTC | 2-Chlorotrityl chloride |
| DBU | 1,8-Diazabicyclo[5.4.0]-7-undecene |
| DCC | N,N'-Dicyclohexylcarbodiimide |
| DCM | Dichloromethane |
| DIC | N,N'-Diisopropylcarbodiimide |
| DIPEA or DIEA | N,N-Diisopropylethylamine |
| DMF | N,N-Dimethylformamide |
| $Et_3N$ | Triethylamine |
| FA | Formic acid |
| Fmoc | Fluorenylmethoxycarbonyl |
| HATU | O-(7-Azabenzotriazol-1-yl)-N,N,N',N'-tetramethyluronium hexafluorophosphate |
| HBTU | O-(Benzotriazol-1-yl)-N,N,N',N'-tetramethyluronium hexafluorophosphate |
| HOAt | 1-Hydroxy-7-azabenzotriazole |
| HFIP | Hexafluoro-2-propanol |
| HOBt | 1-Hydroxybenzotriazole |
| HOOBt | 3,4-Dihydro-3-hydroxy-4-oxo-1,2,3-benzotriazine |
| HOSu | N-Hydroxysuccinimide |
| IPA | Isopropyl alcohol |
| IPAC | Isopropyl acetate |
| NMP | N-Methyl-2-pyrrolidone |
| PyBOP | 1H-Benzotriazol-1-yloxytripyrrolidinophosphonium hexafluorophosphate |
| tBu | t-Butyl |
| TFA | Trifluoroacetic acid |
| TFE | 2,2,2-Trifluoroethanol |
| THF | Tetrahydrofuran |
| Trt | Trityl |
| TsOH | p-Toluenesulfonic acid |
| WSC | 1-[3-(Dimethylamino)propyl]-3-ethylcarbodiimide |

As used herein, the term "amino group-containing compound" refers to a compound having at least one primary or secondary amino group that is free (not protected by a protecting group). Herein, an amino group-containing compound which contains a free primary or secondary amino group protected by a protecting group Q may be called an "amino group-containing compound protected by a protecting group Q".

As used herein, the term "amino acid" includes both natural and unnatural amino acids. As used herein, the term "natural amino acid" refers to Gly (glycine), Ala (alanine), Ser (serine), Thr (threonine), Val (valine), Leu (leucine), Ile (isoleucine), Phe (phenylalanine), Tyr (tyrosine), Trp (tryptophan), His (histidine), Glu (glutamic acid), Asp (aspartic acid), Gln (glutamine), Asn (asparagine), Cys (cysteine), Met (methionine), Lys (lysine), Arg (arginine), and Pro (proline). Examples of the unnatural amino acids include, but are not particularly limited to, β-amino acids, γ-amino acids, D-amino acids, N-substituted amino acids, α,α-disubstituted amino acids, and amino acids having side chains that are different from those of natural amino acids. Amino acids as used herein may have any conformation. There is no particular limitation on the selection of amino acid side chains, but, in addition to a hydrogen atom, they may be freely selected from, for example, an alkyl group, an alkenyl group, an alkynyl group, an aryl group, a heteroaryl group, an aralkyl group, and a cycloalkyl group. Each of the groups may have a substituent, without no particular limitation, and one or two or more substituents may be freely and independently selected from any substituents including, for example, a halogen atom, an O atom, an S atom, an N atom, a B atom, an Si atom, and a P atom. Specifically, examples include an optionally substituted alkyl group, alkenyl group, alkynyl group, aryl group, heteroaryl group, aralkyl group, and cycloalkyl group. In some embodiments, amino acids as used herein may be compounds having a carboxy group and an amino group in the same molecule (even in this case, amino acids also include proline, hydroxyproline, and such). Amino acids as used herein may have a functional group protected by a protecting group. Examples of the functional groups protected by a protecting group include a functional group located on a main chain (an amino group or a carboxy group) and a functional group located on a side chain. Specifically, amino acids as used herein also include, for example, those having an amino and/or carboxy group protected by a protecting group. Amino acids as used herein include those attached to a solid-phase support.

A main chain amino group of an amino acid may be unsubstituted (an NH2 group) or substituted (specifically, an —NHR group, where R represents alkyl, alkenyl, alkynyl, aryl, heteroaryl, aralkyl, or cycloalkyl, which may have a substituent, or a carbon chain attached to the N atom may form a ring with the carbon atom at the position a, as in proline). Substituents of R are selected as with the substituents in the aforementioned amino acid side chains. Such an amino acid having a substituted main chain amino group is herein called an "N-substituted amino acid". Preferred examples of the "N-substituted amino acids" as used herein include, but are not limited to, an N-alkylamino acid, an N-alkyl (C1-6) amino acid, an N-alkyl (C1-3) amino acid, and an N-methylamino acid.

As used herein, the term "amino acid analog" refers to preferably hydroxycarboxylic acid, and more preferably α-hydroxycarboxylic acid. α-Hydroxycarboxylic acid side chains are not particularly limited as in the case of the amino acid side chains, and examples thereof include a hydrogen atom, an alkyl group, an alkenyl group, an alkynyl group, an aryl group, a heteroaryl group, an aralkyl group, and a cycloalkyl group. α-Hydroxycarboxylic acid may have a conformation corresponding to that of an L-amino acid or a D-amino acid. The side chains are not particularly limited and are freely selected from any functional groups including, for example, a halogen atom, an N atom, an O atom, an S atom, a B atom, an Si atom, and a P atom. The number of substituents is not particularly limited and may be one or two or more. For example, the analogs may have an S atom and an additional functional group such as an amino group or a halogen group. β- or γ-Amino acid analogs may have any conformation as in the case of α-amino acid analogs, and their side chains may be selected without particular limitations as in the case of α-amino acid analogs.

"Amino acids" and "amino acid analogs" contained in amino group-containing compounds or peptides as used herein include all isotopes corresponding to each of them. Isotopes of "amino acids" or "amino acid analogs" are those in which at least one atom is replaced with an atom having the same atomic number (proton number) and different mass number (the total number of protons and neutrons). Examples of isotopes contained in "amino acids" or "amino acid analogs" constituting amino group-containing compounds or peptides of the present invention include a hydrogen atom, a carbon atom, a nitrogen atom, an oxygen atom, a phosphorus atom, a sulfur atom, a fluorine atom, and a chlorine atom, including 2H and 3H; 13C and 14C; 15N; 17O and 18O; 32P; 35S; 18F; and 36Cl, respectively.

As used herein, the term "peptide" refers to a substance in which two or more amino acids and/or amino acid analogs are linked to each other by an amide bond and/or an ester bond. In a peptide having a cyclic structure, a mode of binding at the cyclization site is not particularly limited and may be a bond other than an amide or ester bond. Preferred examples of the modes of binding at the cyclization site include a covalent bond such as an amide bond, a carbon-carbon bond, a disulfide bond, an ester bond, a thioester bond, a thioether bond, a lactam bond, a bond through a triazole structure, and a bond through a fluorophore structure, with an amide bond being particularly preferred due to high metabolic stability. Functional groups to be used for cyclization such as a carboxylic acid group and an amino group may be located on the main chains or on the side chains, and their positions are not particularly limited as long as they can allow cyclization. As used herein, the term "mode of binding at the cyclization site" refers to a mode of binding at the site where a cyclization occurs by cyclization reaction.

Amino group-containing compounds and peptides as used herein may have functional groups protected by protecting groups, unprotected functional groups, or both. Examples of the functional groups to be protected by protecting groups include a functional group located on the main chains (such as an amino group or a carboxy group) and a functional group located on the side chains. Specifically, amino group-containing compounds and peptides as used herein also include amino group-containing compounds and peptides in which some or all of functional groups such as amino and carboxy groups are protected by protecting groups. Peptides as used herein include amino group-containing compounds and peptides attached to a solid-phase support. Amino group-containing compounds and peptides as used herein include amino group-containing compounds and peptides in which some of the functional groups are derivatized to decrease the reactivity. For example, amino group-containing compounds and peptides as used herein also include compounds in which piperidinamide or pyrrolidinamide is formed by a reaction between the peptide C-terminal carboxy group with piperidine or pyrrolidine.

Herein, when an amino acid, an amino acid analog, a peptide, amino group-containing compound, or the like has the amino terminus and/or the carboxy terminus, the amino terminus is defined as the N-terminus and the carboxy terminus is defined as the C-terminus. Even if the amino and/or carboxy termini of an amino acid, a peptide, an amino group-containing compound, or the like are protected by a protecting group, attached to a solid-phase support, or derivatized to decrease the reactivity, such respective termini are included in the definitions of the N-terminus and the C-terminus.

As used herein, if in terms of amino acids or peptides, the term "main chain" refers to a chain linking between their C and N-termini, and a main chain of an amino group-containing compound is also defined accordingly. As used herein, the term "side chain" refers to an atomic group branched from a main chain and containing at least one carbon atom. For example, the side chain of H2N—CH(R)—COOH is R (but this does not apply to R containing no carbon atom). For example, the side chains of the peptide H2N—CH(R21)-CON(R22)-CH(R23)-CONH—CR24(R25)-COOH are R21, R22, R23, R24, and R25 (but this does not apply to R21, R22, R23, R24, or R25 containing no carbon atom).

As used herein, the term "protection" refers to temporarily converting a highly reactive functional group, a functional group undesirable to react, or the like to a derivative (by attaching some atomic group thereto) to decrease the reactivity.

As used herein, the term "protecting group" refers to an atomic group used for temporarily protecting a highly reactive functional group such as an amino group, a carboxy group, or a hydroxy group. Representative examples of the protecting groups include a fluorenylmethoxycarbonyl (Fmoc) group, an acetyl group, a benzyl group, a benzoyl group, a t-butoxycarbonyl (Boc) group, a t-butyl group, a t-butyldimethyl group, a silyl group, a trimethylsilylethyl group, an N-phthalimidyl group, a trimethylsilylethyloxycarbonyl group, and a carbamate group. Protecting groups can be used for protecting, for example, reactive functional groups such as an amino group, a carboxy group, or a hydroxy group. Various different protecting groups can be used according to the condition and purpose of the reaction. It is possible to use, as a protecting group for a hydroxy group, an acetyl group, a benzyl group, a silyl group, or a derivative thereof, or such; as a protecting group for an amino group, an Fmoc group, an acetyl group, a benzyloxycarbonyl (Cbz) group, a t-butoxycarbonyl (Boc) group, or a derivative thereof, or such; and as a protecting group for a carboxy group, a benzyl group, a t-butyl group, or a derivative thereof, or such. As a protecting group for an aminooxy group and an N-alkylaminooxy group, a trimethylsilylethyloxycarbonyl group, a derivative thereof, or such can be used.

In some embodiments, examples of the protecting groups in the present disclosure include protecting groups that protect an amino group, a carboxy group, a hydroxy group, a thiol group, a guanidino group, an amido group, an imidazole group, or an indole group. In some embodiments, examples of the protecting groups in the present disclosure also include a "main chain protecting group" and a "side chain protecting group". As used herein, a "main chain protecting group" refers to a protecting group that protects a functional group at a terminus of a main chain of an amino acid, an amino acid analog, a peptide, or an amino group-containing compound (typically an amino group at the N-terminus (amino terminus) and/or a carboxy group at the C-terminus (carboxy terminus)). As used herein, a "side chain protecting group" refers to a protecting group that protects a side chain functional group of an amino acid, a peptide, or an amino group-containing compound.

As used herein, the term "deprotection" refers to removing the protecting group to bring the functional group back into the original functional group as in before protected. As used herein, the term "deprotecting agent" refers to a reagent used for deprotection.

As used herein, the phrase "allowing . . . to coexist (allowing coexistence)" refers to allowing substances of interest to be present in the same reaction system, and such substances may be present in contact with or separately from each other. For example, allowing A and B to coexist may be performed by mixing A with B or by mixing a mixture containing A, which is produced as a consequence of some reaction, with B.

As used herein, the phrase "amino acid or peptide having an amino group protected by a protecting group P" refers to an amino acid having an amino group protected by a protecting group P, or a peptide having an amino group protected by a protecting group P.

As used herein, the term "alkyl" refers to a monovalent group derived by removing any one hydrogen atom from an aliphatic hydrocarbon and covers a subset of hydrocarbyl or hydrocarbon group structures that contain hydrogen and carbon atoms, but do not contain a heteroatom (which refers to an atom other than carbon and hydrogen atoms) or an unsaturated carbon-carbon bond in the backbone. The alkyl groups include linear or branched groups. The alkyl groups are alkyl groups having 1 to 20 carbon atoms (C1-20; hereinafter, "Cp-q" means that the number of carbon atoms is p to q; the terms "Cp-q alkyl" and "alkyl (Cp-q)" are synonymously used herein), preferred examples of which include a C1-10 alkyl group, a C1-6 alkyl group, a C1-5 alkyl group, a C1-4 alkyl group, and a C1-3 alkyl group. Specific examples of alkyl include methyl, ethyl, propyl, butyl, pentyl, hexyl, isopropyl, tert-butyl group, sec-butyl group, 1-methylpropyl group, 1,1-dimethylpropyl group, 2,2-dimethylpropyl, 1,2-dimethylpropyl, 1,1,2-trimethylpropyl, 1,2,2-trimethylpropyl, 1,1,2,2-tetramethylpropyl, 1-methylbutyl, 2-methylbutyl, 3-methylbutyl, 1,1-dimethylbutyl, 1,2-dimethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, isopentyl, neopentyl, and isooctyl.

As used herein, the term "alkenyl" refers to a monovalent group having at least one double bond (two adjacent SP2 carbon atoms). Depending on the configuration of the double bond and the substituent (if present), the geometry of the double bond can be an entgegen (E) or zuzammen (Z) configuration or a cis or trans configuration. Examples of alkenyl include linear or branched ones, including linear chains containing internal olefins. Preferred examples include C2-10 alkenyl, with C2-6 alkenyl and C2-4 alkenyl being more preferred. Specific examples of such alkenyl include vinyl, allyl, 1-propenyl, 2-propenyl, 1-butenyl, 2-butenyl (including cis and trans), 3-butenyl, pentenyl, and hexenyl.

As used herein, the term "alkynyl" refers to a monovalent group having at least one triple bond (two adjacent SP carbon atoms). Examples include linear or branched alkynyl groups, including internal alkylenes. Preferred examples include C2-10 alkynyl, with C2-6 alkynyl and C2-4 alkynyl being more preferred. Specific examples of alkynyl include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

As used herein, the term "cycloalkyl" refers to a saturated or partially saturated cyclic monovalent aliphatic hydrocarbon group, including single rings, bicyclo rings, and spiro rings. A preferred example is C3-10 cycloalkyl. The cycloalkyl groups may be partially unsaturated. Specific examples of cycloalkyl include cyclopropyl, cyclobutyl, cyclopentyl, cyclohexyl, cycloheptyl, cyclooctyl, and bicyclo[2.2.1]heptyl.

As used herein, the term "aryl" refers to a monovalent aromatic hydrocarbon ring, a preferred example of which is C6-10 aryl. Specific examples of aryl include phenyl and naphthyl (e.g., 1-naphthyl or 2-naphthyl).

As used herein, the term "heteroaryl" refers to a monovalent aromatic ring group containing preferably 1 to 5 heteroatoms in the ring-forming atoms (herein also called "in the ring"), which may be partially saturated. The ring may be a single ring or two fused rings (such as bicyclic heteroaryl obtained by fusion with benzene or monocyclic heteroaryl). The number of the ring-forming atoms is preferably 5 to 10 (5- to 10-membered heteroaryl). Specific examples of heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

The term "arylalkyl (aralkyl)" as used herein refers to a group containing both aryl and alkyl, for example, a group in which at least one hydrogen atom of the abovementioned alkyl is replaced with aryl, a preferred example of which is "C5-10 aryl-C1-6 alkyl". An example is benzyl.

Halogen atoms as used herein include F, Cl, Br, and I, preferred examples of which include F or Cl. Substituents containing a halogen atom include, but are not limited to, fluoro (—F), chloro (—Cl), bromo (—Br), and iodo (—I). Examples include a halogen-substituted alkyl group, cycloalkyl group, alkenyl group, alkynyl group, aryl group, heteroaryl group, or aralkyl group, having one or more the above substituents. More specific examples include fluoroalkyl, difluoroalkyl, and trifluoroalkyl.

O atom-containing substituents include groups such as hydroxy (—OH), oxy (—OR), carbonyl (—C=O—R), carboxy (—CO2H), oxycarbonyl (—C=O—OR), carbonyloxy (—O—C=O—R), thiocarbonyl (—C=O—SR), carbonylthio (—S—C=O—R), aminocarbonyl (—C=O—NHR), carbonylamino (—NH—C=O—R), oxycarbonylamino (—NH—C=O—OR), sulfonylamino (—NH—SO2-R), aminosulfonyl (—SO2-NHR), sulfamoylamino (—NH—SO2-NHR), thiocarboxyl (—C(=O)—SH), and carboxylcarbonyl (—C(=O)—CO2H).

Examples of oxy (—OR) include alkoxy, cycloalkoxy, alkenyloxy, alkynyloxy, aryloxy, heteroaryloxy, and aralkyloxy. The alkoxy is preferably C1-4 alkoxy and C1-2 alkoxy, and particularly preferably methoxy or ethoxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl (examples of which include C1-6 or C1-4 alkylaminocarbonyl, in particular, ethylaminocarbonyl and methylaminocarbonyl), cycloalkylaminocarbonyl, alkenylaminocarbonyl, alkynylaminocarbonyl, arylaminocarbonyl, heteroarylaminocarbonyl, and aralkylaminocarbonyl. Additional examples include compounds in which the H atom bonded to the N atom in —C=O—NHR is further substituted with alkyl, cycloalkyl, alkenyl, alkynyl, aryl, heteroaryl, or aralkyl.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include compounds in which the H atom bonded to the N atom in —NH—C=O—R is further substituted with alkyl, cycloalkyl, alkenyl, alkynyl, aryl, heteroaryl, or aralkyl.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include compounds in which the H atom bonded to the N atom in —NH—C=O—OR is further substituted with alkyl, cycloalkyl, alkenyl, alkynyl, aryl, heteroaryl, or aralkyl.

Examples of sulfonylamino (—NH—SO2-R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include compounds in which the H atom bonded to the N atom in —NH—SO2-R is further substituted with alkyl, cycloalkyl, alkenyl, alkynyl, aryl, heteroaryl, or aralkyl.

Examples of aminosulfonyl (—SO2-NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include compounds in which the H atom bonded to the N atom in —SO2-NHR is further substituted with alkyl, cycloalkyl, alkenyl, alkynyl, aryl, heteroaryl, or aralkyl.

Examples of sulfamoylamino (—NH—SO2-NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. The two H atoms bonded to the N atoms in —NH—SO2-NHR may be further substituted with substituents independently selected from the group consisting of alkyl, cycloalkyl, alkenyl, alkynyl, aryl, heteroaryl, and aralkyl, and these two substituents may form a ring.

S atom-containing substituents include groups such as thiol (—SH), thio (—S—R), sulfinyl (—S=O—R), sulfonyl (—SO2-R), and sulfo (—SO3H).

Examples of thio (—S—R) include alkylthio, cycloalkylthio, alkenylthio, alkynylthio, arylthio, heteroarylthio, and aralkylthio.

Examples of sulfonyl (—SO2-R) include alkylsulfonyl, cycloalkylsulfonyl, alkenylsulfonyl, alkynylsulfonyl, arylsulfonyl, heteroarylsulfonyl, and aralkylsulfonyl.

Examples of N atom-containing substituents include groups such as azido (—N3, also called "azido group"), cyano (—CN), primary amino (—NH2), secondary amino (—NHR; also called monosubstituted amino), tertiary amino (—NR(R'); also called disubstituted amino), amidino (—C (=NH)—NH2), substituted amidino (—C(=NR)—NR'R"), guanidino (—NH—C(=NH)—NH2), substituted guanidino (—NR—C(=NR''')—NR'R"), aminocarbonylamino (—NR—CO—NR'R"), pyridyl, piperidino, morpholino, and azetidinyl.

Examples of secondary amino (—NHR; monosubstituted amino) include alkylamino, cycloalkylamino, alkenylamino, alkynylamino, arylamino, heteroarylamino, and aralkylamino.

Examples of tertiary amino (—NR(R'); disubstituted amino) include amino groups having any two substituents each independently selected from alkyl, cycloalkyl, alkenyl, alkynyl, aryl, heteroaryl, and aralkyl, such as alkyl(aralkyl)amino, where any two such substituents may form a ring. Specific examples include dialkylamino, in particular, C1-6 dialkylamino, C1-4 dialkylamino, dimethylamino, and diethylamino. The term "Cp-q dialkylamino group" as used herein refers to an amino group substituted with two Cp-q alkyl groups, where the two Cp-q alkyl groups may be the same or different.

Examples of substituted amidino (—C(=NR)—NR'R") include groups in which three substituents R, R', and R" on the N atoms are each independently selected from alkyl, cycloalkyl, alkenyl, alkynyl, aryl, heteroaryl, and aralkyl, such as alkyl(aralkyl)(aryl)amidino.

Examples of substituted guanidino (—NR—C(=NR''')—NR'R") include groups in which R, R', R", and R''' are each independently selected from alkyl, cycloalkyl, alkenyl, alkynyl, aryl, heteroaryl, and aralkyl, or groups in which these substituents form a ring.

Examples of aminocarbonylamino (—NR—CO—NR'R") include groups in which R, R', and R" are each independently selected from a hydrogen atom, alkyl, cycloalkyl, alkenyl, alkynyl, aryl, heteroaryl, and aralkyl, or groups in which these substituents form a ring.

Herein, amino acids and amino acid analogs constituting amino group-containing compounds and peptides may be called amino acid residues and amino acid analog residues, respectively.

In some embodiments, one or more functional groups contained in an amino acid, a peptide, or an amino group-containing compound of the present disclosure may be protected by a protecting group. The functional groups may include main chain and side chain functional groups. As used herein, the term "main chain functional group" refers to a functional group located at a terminus of a main chain. As used herein, the term "side chain functional group" refers to a functional group contained in a side chain.

Examples of the main chain functional groups of the present disclosure include, but are not limited to, an amino group and a carboxy group. Examples of the side chain functional groups of the present disclosure include, but are not limited to, an amino group, a carboxy group, a hydroxy group, a thiol group, a guanidino group, a hydroxyphenyl group, an indole group, an imidazole group, and an amido group.

The methods of the present disclosure are preferably performed in the presence of an appropriate protecting group. Generally, such an appropriate protecting group is a group of any type acting to prevent an atom or moiety to which it is attached, such as oxygen or nitrogen, from being involved in an undesirable reaction in the process of synthesizing and processing peptides. Examples of the protecting groups include protecting groups that protect an amino group, a carboxy group, a hydroxy group, a thiol group, a guanidino group, a hydroxyphenyl group, an indole group, an imidazole group, and an amido group. Examples of the protecting groups of the present disclosure also include protecting groups for main chain functional groups (C-terminal and N-terminal protecting groups) and protecting groups for side chain functional groups in amino acids, peptides, or amino group-containing compounds.

In some embodiments, some or all of the side chain functional groups in an amino acid, a peptide, or an amino group-containing compound of the present disclosure may be protected by protecting groups throughout the course of peptide chain elongation reaction. In some embodiments, when an amino acid, a peptide, or an amino group-containing compound is attached to a solid-phase support through a side chain functional group, side chain functional groups other than the functional group used for attachment to the support may be protected by protecting groups throughout the course of peptide chain elongation reaction. In some embodiments, a carboxy group on the C-terminal side of an amino acid, a peptide, or an amino group-containing compound (e.g., the C-terminal carboxy group) may be protected by a protecting group or may be derivatized to decrease the reactivity (for example, the C-terminal carboxy group may be reacted with piperidine or pyrrolidine to form piperidinamide or pyrrolidinamide).

In some embodiments, protecting groups selected for side chain functional groups or optionally for the C-terminal carboxy group in an amino acid, a peptide, and/or an amino group-containing compound of the present disclosure is preferably one which cannot be removed under conditions where the N-terminal amino group protected by a protecting group is deprotected. When the protecting group for the N-terminal amino group is removed with a base, the protecting groups selected for the side chain functional groups and/or for the C-terminal carboxy group are preferably those which cannot be removed with a base. In some embodiments, protecting groups removable by acid hydrolysis may be used for the side chain functional groups and/or the C-terminal carboxy group when the N-terminal amino group is protected by an Fmoc group. Examples of the protecting groups that cannot be removed with a base and/or the protecting groups removable by acid hydrolysis include tBu, trityl (Trt), 2-phenylisopropyl (2-PhiPr), 2-chlorotrityl (2-Cl-Trt), allyl, and benzyl. The protecting groups may be appropriately selected from these protecting groups according to the chemical structure of the side chain.

In some embodiments, the protecting groups that cannot be removed with a base are not particularly limited, and may be at least one protecting group selected from the group consisting of: tBu, Trt, 2-PhiPr, 2-Cl-Trt, allyl, and benzyl as protecting groups for a carboxy group; Boc, benzyloxycarbonyl (CbZ), allyloxycarbonyl (Alloc), o-NBS, 1-(4,4-dimethyl-2,6-dioxocyclohex-1-ylidene)-3-ethynyl (Dde), 1-(4,4-dimethyl-2,6-dioxocyclohex-1-ylidene)-3-methylbutyl (ivDde), and tfa as protecting groups for an amino group; Bn, tBu, Trt, tetrahydropyranyl (THP), methoxymethyl (MOM), and silyl represented by a tert-butyldimethylsilyl group (TBDMS) as protecting groups for a hydroxy group (an alkyl alcohol represented by Ser, Thr, or Hyp); and Bn, tBu, Trt, THP, silyl represented by TBDMS, and Boc, CbZ, 2-Cl-Trt, and allyl as protecting groups for a hydroxy group (a phenol represented by Tyr).

In some embodiments, any one or more side chains in an amino acid, a peptide, and/or an amino group-containing compound of the present disclosure may be protected by a standard protecting group such as t-butyl (tBu), trityl (Trt), and t-butyloxycarbonyl (Boc). Side chain protecting groups of the present disclosure include a tBu group for Tyr, Thr, Ser, and Asp; a Trt group for His, Gln, and Asn; and a Boc group for Lys and Trp.

In some embodiments, amino group-containing compounds of the present disclosure may have either one of a free primary amino group or a free secondary amino group. In some embodiments, the other functional groups in the amino group-containing compounds may be protected by protecting groups, may be used for attachment to a solid-phase support, or may be derivatized to decrease the reactivity. In some embodiments, amino group-containing compounds of the present disclosure may be compounds having one or at least one free secondary amino group. Examples of the secondary amino groups of the present disclosure include N-alkylamino groups, preferably N-alkyl (C1-6) amino groups and N-alkyl (C1-3) amino groups, and particularly preferably an N-methylamino group.

In some embodiments, amino group-containing compounds of the present disclosure may be attached to a solid-phase support. A mode of attachment to the solid-phase support is not particularly limited. For example, the amino group-containing compounds may be attached thereto through a functional group possessed by the compounds. Such a functional group is, appropriately selected from a carboxy group, a hydroxy group, an amino group, a thiol group, and the like according to that possessed by the amino group-containing compounds, and a preferable example is a carboxy group. In some embodiments, examples of the modes of attachment of the amino group-containing compounds to the solid-phase support include an ester bond, an ether bond, and an amide bond.

In some embodiments, amino group-containing compounds of the present disclosure may be amino acids or peptides having at least one free primary amino group or free secondary amino group. In some embodiments, the peptides may be, but are not limited to, peptides in which 2 to 49, 2 to 29, or 2 to 19 amino acids and/or amino acid analogs are sequentially linked, or peptides in which 2, 3, 4, 5, 6, 7, 8, 9, 10, 11, 12, 13, 14, or 15 amino acids and/or amino acid analogs are sequentially linked. Even in this case, a mode of attachment to a solid-phase support in some embodiments is not particularly limited. For example, the amino group-containing compounds may be attached to a solid-phase support through a main chain or side chain functional group thereof. In some embodiments, the amino group-containing compounds may be attached to a solid-phase support through a main chain or side chain functional group located on its C-terminal side. The "C-terminal side" as used herein is not limited to the amino acid located at the C-terminus, and includes, for example, an amino acid or amino acid analog located at the first, second, or third position from the C-terminus. In some embodiments, a functional group possessed by an amino acid or amino acid analog at the C-terminus of a peptide or by an amino acid or amino acid analog located at the second or third position from the C-terminus may be used for attachment to a solid-phase support. For example, in some embodiments, a main chain or side chain carboxy group of an amino acid or of the amino acid located at the C-terminus of a peptide may be used. In other embodiments, when a peptide has, for example, Asp at the second position from the C-terminus, the side chain carboxy group of the Asp can be used for attachment to a solid-phase support. In this manner, various methods can be used for attachment to a solid-phase support without particular limitations.

In some embodiments, an amino group-containing compound and/or a peptide of the present disclosure may contain one or more, two or more, or three or more N-substituted amino acids. Examples of the N-substituted amino acids include N-alkylamino acids, preferably N-alkyl (C1-6) amino acids and N-alkyl (C1-3) amino acids, and more preferably N-methylamino acids.

In some embodiments, an amino group-containing compound of the present disclosure is represented by the following general formula (I):

$$HR^{11}N\text{—}X\text{-}D \quad (I)$$

wherein

HR$^{11}$N—X— represents an amino acid or peptide residue,

HR$^{11}$N— represents the N-terminal amino group of an amino acid or peptide,

R$^{11}$ represents H or an alkyl group, and

D represents a solid-phase support or a protecting group, attached to the C-terminal side of X.

In some embodiments, R11 mentioned above may be a C1-6 alkyl group, may be a C1-3 alkyl group, or may be a methyl group. In some embodiments, HR11N—X— mentioned above may be an amino acid, or a peptide made with amide bond and/or ester bond linkage, or may be a residue of a peptide made with only amide bond linkage. In some embodiments, D mentioned above may be a solid-phase support or a protecting group, attached to the carboxy group on the C-terminal side of X, and is particularly preferably a solid-phase support.

Solid-phase supports of any type that can be utilized for solid-phase peptide synthesis can be used as solid-phase supports of the present disclosure. In some embodiments, the solid-phase supports may contain one or more types of polymers, and such polymers may be homopolymers or copolymers. The solid-phase supports of the present disclosure may contain a polymer such as a polyamide, polysulfamide, substituted polyethylene, polyethylene glycol, phenol resin, polysaccharide, or polystyrene, or a resin containing one type of polymer or a combination of two or more types of polymers selected from the above polymers. The solid-phase supports may contain a divinylbenzene-crosslinked polystyrene resin, a crosslinked polyethylene glycol resin, or the like. The solid-phase supports may contain linking moieties to which amino group-containing compounds can be attached, and from which synthesized peptides can be cleaved under desired conditions, and thereby releasing the peptides from the solid-phase supports. In some embodiments, the solid-phase supports of the present disclosure may be solid-phase supports that cannot be removed with a base. In some embodiments, the solid-phase supports of the present disclosure may contain a linker that cannot be cleaved with a base, and are preferably a linker that cannot be cleaved with a base X. In some embodiments, the solid-phase supports of the present disclosure may contain linkers that are photocleavable, are cleavable with an acid (especially a weak acid (such as TFA or acetic acid)), are cleavable with hydrofluoric acid (HF), are cleavable with a fluoride ion, are reductively cleavable, are cleavable with Pd(O), are nucleophilically cleavable, or are radically cleavable. The linkers of the present disclosure may be selected according to the structure on the C-terminal side or the like of the peptides cleaved from the solid-phase supports. For example, a linker containing a hydroxymethylphenoxy group, a linker containing a trityl group, particularly a linker containing a 2-chlorotrityl chloride group, or the like can be used to obtain a peptide having a carboxy group on the C-terminal side. The linkers of the present disclosure are preferably linkers cleavable with an acid. The solid-phase supports may contain any of the above linkers and polymers. In some embodiments, the linking moieties may be cleavable under conditions where the amino group at the N-terminus of the main chain and/or the side chain functional groups of the peptides to be cleaved are still substantially entirely protected. In some embodiments, the linking moieties may be cleaved simultaneously with removal of the protecting groups for the side chain functional groups of the peptides to be cleaved.

In some embodiments, the solid-phase supports of the present disclosure may be an acid-sensitive solid-phase support. As used herein, the term "acid-sensitive solid-phase support" refers to a solid-phase support containing a linker cleavable with an acid. Examples of the acid-sensitive solid-phase supports include acid-sensitive solid-phase supports containing a trityl group, and more preferably solid-phase supports containing a trityl group having a pendant chlorine group, such as a 2-chlorotrityl chloride (2-CTC) resin. Examples of other available solid-phase supports include a trityl chloride resin, a 4-methyltrityl chloride resin, and a 4-methoxytrityl chloride resin. The solid-phase supports particularly preferably have a linker determined to have an acid sensitivity of "H (<5% TFA in DCM)" according to Solid-Phase Synthesis Handbook (published by Merck Ltd. on May 1, 2002), and can be appropriately selected depending on a functional group of an amino acid to be used. For example, when a carboxy group (a main chain carboxy group, or a side chain carboxy group represented by Asp or Glu) or a hydroxy group on an aromatic ring (a phenol group represented by Tyr) is used as the amino acid functional group, a trityl chloride resin (Trt resin) or 2-chlorotritylchloride resin (Clt resin) is preferably used as a resin. When an aliphatic hydroxy group (an aliphatic alcohol group represented by Ser or Thr) is used as the amino acid functional group, a trityl chloride resin (Trt resin), a 2-chlorotrityl chloride resin (Clt resin), or a 4-methyltrityl chloride resin (Mtt resin) is preferably used as a resin. The type of the polymers composing the resin is also not particularly limited. Either a 100-200 mesh resin or a 200-400 mesh resin may be used as a resin composed of polystyrene. Although the crosslinking rate is also not particularly limited, a 1% DVB (divinylbenzene)-crosslinked resin is preferred. The amount and rate of loading of the amino acids, peptides, or amino group-containing compounds on the solid-phase supports are not particularly limited.

In some embodiments, amino acids, peptides, or amino group-containing compounds having amino groups protected by protecting groups may be loaded on solid-phase supports by chemically reacting linkers of the solid-phase supports with the carboxy groups that are located at the C-terminus of the amino acids, peptides, or amino group-containing compounds and are free or converted to active esters. Here, the free carboxy groups may be either a main chain carboxy group or a side chain carboxy group (such as Asp or the like side chain) of the amino acids, peptides, or the like. Instead of the carboxy groups, main chain or side chain functional groups (a free OH or SH group) located on the C-terminal side of the amino acids, peptides, or amino group-containing compounds having amino groups protected by protecting groups may be used for attachment to the solid-phase supports.

In some embodiments, the protecting groups for the amino groups of the amino acids, peptides, or amino group-containing compounds loaded on the solid-phase supports may be removed with a deprotecting agent (such as a base) to expose the amino groups. The base used here is not particularly limited, and a deprotecting agent generally used for peptide synthesis can be used (illustrative deprotecting agents are described in the following document: Amino Acid-Protecting Groups (Chem. Rev. 2009, 109, 2455-2504)). Examples of deprotecting agents include amines, bases having an amidine backbone, and bases having a guanidine backbone. Such amines are preferably secondary amines, specific examples of which include piperidine, morpholine, pyrrolidine, and piperazine. Specific examples of the bases having an amidine backbone include 1,8-diazabicyclo[5.4.0]undec-7-ene (DBU) and 1,5-diazabicyclo[4.3.0]-5-nonene (DBN). Specific examples of the bases having a guanidine backbone include 1,1,3,3-tetramethylguanidine, 7-methyl-1,5,7-triazabicyclo[4.4.0]dec-5-ene (MTBD), and 1,5,7-triazabicyclo[4.4.0]dec-5-ene (TBD).

Peptide chains can be elongated by condensation of the exposed amino groups with the carboxy groups of amino acids or peptides having amino groups protected by a protecting group P to form an amide bond. In the present disclosure, amino acids or peptides having protected amino groups preferably have carboxy groups that are free or converted to active esters.

In some embodiments, amino group-containing compounds of the present disclosure may have carboxy groups protected by protecting groups, where all carboxy groups may be protected by protecting groups, or the functional groups on the C-terminal side may be protected by protecting groups. In some embodiments, the protecting groups that protect such carboxy groups may be protecting groups that cannot be removed with a base. In some embodiments, in amino group-containing compounds of the present disclosure, the C-terminal main chain functional group may be protected by a protecting group. In some embodiments, the main chain and side chain functional groups on the C-terminal side may be protected by protecting groups. In some embodiments, in amino group-containing compounds of the present disclosure, only one primary or secondary amino group may exist in a free state and the other functional groups may all be protected by protecting groups.

In some embodiments, amino acids or peptides having amino groups protected by a protecting group P, which is used in step (b) of the present disclosure, may be amino acids or peptides having at least one, preferably one, carboxy group that is free (i.e., not protected by a protecting group) or converted to an active ester. The carboxy group may be a main chain carboxy group or a side chain carboxy group, but is preferably a main chain carboxy group. The other reactive functional groups in the amino acids or peptides may be protected by protecting groups. Use of such amino acids or peptides allows the carboxy group to form an amide bond with the amino group of amino group-containing compounds, thereby elongating peptide chains. Protecting groups for side chain functional groups may be appropriately selected according to the chemical structure of the side chains.

In some embodiments, "protecting group P" and "protecting group Q" of the present disclosure may be protecting groups of the same or different types. In some embodiments, at least one protecting group selected from the group consisting of protecting groups P and Q or both protecting groups of the present disclosure may be protecting groups for amino groups. Examples of the amino groups include a side chain amino group or an N-terminal amino group, with an N-terminal amino group being preferred. In some embodiments, at least one protecting group selected from the group consisting of protecting groups P and Q or both protecting groups of the present disclosure are preferably protecting groups removable with a base, and particularly preferably protecting groups removable with a base X. In some embodiments, protecting groups P and Q of the present disclosure may be protecting groups that cannot be removed with a base Y. Protecting groups P and Q of the present disclosure may be protecting groups that cannot be removed when the peptides are cleaved from the solid-phase supports and/or when the side chain protecting groups of the peptides are removed, and in particular may be protecting groups that cannot be removed with an acid.

In some embodiments, protecting groups P and/or Q of the present disclosure may be protecting groups having an Fmoc backbone. Such protecting groups having an Fmoc backbone include a protecting group having a structure represented by the following general formula II:

Chemical formula 1

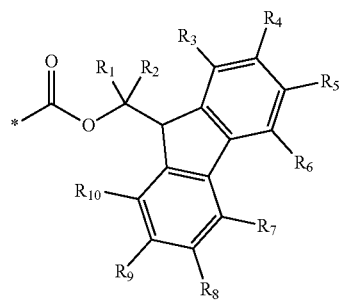

(II)

wherein
$R_1$ to $R_{10}$ each independently represent a hydrogen atom, an alkyl group, an aryl group, or a halogen group, and
* represents the point of attachment to an amino group of an amino acid or peptide.

In some embodiments, examples of the protecting groups having an Fmoc backbone of the present disclosure include an Fmoc group (the general formula II, where R1 to R10 are all H), a 2,7-di-tert-butyl-Fmoc group (the general formula II, where R4=tBu, R9=tBu, and R1 to R3, R5 to R8, and R10=H), an Fmoc(2F) group (the general formula II, where R4=F and R1 to R3 and R5 to R10=H), a mio-Fmoc group (the general formula II, where R4=isooctyl and R1 to R3 and R5 to R10=H), and a dio-Fmoc group (the general formula II, where R4=isooctyl, R9=isooctyl, and R1 to R3, R5 to R8, and R10=H), with an Fmoc group being particularly preferred.

Use of protecting groups having an Fmoc backbone for protecting amino groups allows the protecting groups (such as an Fmoc group) for the amino groups to be selectively removed from the peptides while retaining the protecting groups for the side chains of the peptides, linkage to the solid-phase supports, and such. It is also possible to remove the protecting groups for the side chains of the peptides or the like and cleave the site of linking to the solid-phase supports while retaining the protecting groups having an Fmoc backbone.

When the Fmoc strategy is used, amino acids or peptides that can be used are, for example, those in which the main chain amino groups are protected by protecting groups having an Fmoc backbone, side chain functional groups are protected as necessary by protecting groups that cannot be removed with a base (such as piperidine or DBU), and the main chain carboxy groups are free (unprotected) or converted to active esters. When the amino acids or peptides have side chain functional groups, the functional groups are preferably protected by protecting groups. When the side chain functional groups are protected by protecting groups, it is possible to use well-known protecting groups that can be removed under any conditions. For example, the protecting groups described in the following documents i) and ii) which meet the above conditions may also be employed as side chain protecting groups.

Non-Patent Literature i) Greene's Protective Groups in Organic Synthesis, 5th Edition;
Non-Patent Literature ii) Chemical Reviews, 2009, 109 (6), 2455-2504.

A "removable protecting group", which is generally used in the art in combination with a deprotecting agent, is understood to be a protecting group removable with the deprotecting agent. Likewise, when the term "removable" is used in the context of a solid-phase support in association with a reagent which is generally used for cleaving a peptide from a certain solid-phase support, the solid-phase support is understood to be a solid-phase support removable from the peptide attached thereto. For example, it is understood that a protecting group having an Fmoc backbone (such as an Fmoc group) is a protecting group removable with a base, and a 2-chlorotrityl chloride (2-CTC) resin is a solid-phase support removable with an acid. The phrase that a protecting group "cannot be removed" may mean that a removed protecting group is not detected under common deprotection conditions used in the art. The phrase that a solid-phase support "cannot be removed" may mean that a peptide removed from a solid-phase support is not detected under common reaction conditions used in the art. For example, a protecting group or a solid-phase support neither of which is removable with a base refers to a protecting group (such as Boc or tBu) or a solid-phase support (such as a 2-CTC resin) neither of which is intended to be removed during removal of a protecting group such as an Fmoc group with a base when used in common peptide synthesis.

In some embodiments, amino groups protected by protecting groups P and/or Q may be either a main chain amino group (N-terminal amino group) or side chain amino groups of amino acids or peptides and can be selected according to the structure of desired peptides, but preferably be a main chain amino group. In some embodiments, amino groups protected by protecting groups P and/or Q may be primary or secondary amino groups.

In some embodiments, protecting groups P and/or Q of the present disclosure may be N-terminal protecting groups (protecting groups that protect the N-terminal amino groups) for amino acids, peptides, or the like. Such N-terminal protecting groups contain chemical moieties coupled with the α-amino groups of amino acids, the N-terminal amino groups of peptides, or the like. Typically, the N-terminal protecting groups of growing peptide chains are removed by deprotection reaction before supplying a subsequent amino acid to be added to the peptide chains. In this case, the N-terminus of the subsequent amino acid may be protected by an N-terminal protecting group. In some embodiments, the N-terminal protecting groups may be retained when synthesized peptide chains are cleaved from solid-phase supports. The N-terminal protecting groups may be selected taking into consideration various factors such as the type of a peptide synthesis method to be conducted, processing applied to peptides, and desired intermediates or final products.

Side chain protecting groups of the present disclosure may be protecting groups that cannot be removed during deprotection of the N-terminal amino groups in a peptide synthesis process. In this case, different types of protecting groups are used for the N-terminal amino groups and side chain functional groups.

Side chain protecting groups act to protect some side chains of amino acids, peptides, or amino group-containing compounds from reactions with chemical substances used in peptide synthesis, processing, or the like steps. Side chain protecting groups may be selected taking into consideration various factors such as the type of a peptide synthesis method to be conducted, processing applied to peptides, and desired intermediates or final products.

In some embodiments, a base X of the present disclosure may be a deprotecting agent for an amino group protected by a protecting group. In some embodiments, the protecting group may be a protecting group Q or P. In some embodiments, the base X may be a deprotecting agent generally used in peptide synthesis. In some embodiments, the conjugate acid of the base X may have a pKa of 10.0 or more, preferably 11.0 or more, and more preferably 11.5 or more. In some embodiments, the base X may be an organic base. The base X may be at least one base selected from the group consisting of amines, bases having an amidine backbone, and bases having a guanidine backbone, and is particularly preferably bases having an amidine backbone. Examples of the bases having an amidine backbone include DBU and DBN. Amines mentioned above are preferably secondary amines, specific examples of which include piperidine, morpholine, pyrrolidine, and piperazine. Examples of the bases having a guanidine backbone include 1,1,3,3-tetramethylguanidine, 7-methyl-1,5,7-triazabicyclo[4.4.0]dec-5-ene (MTBD), and 1,5,7-triazabicyclo[4.4.0]dec-5-ene (TBD). Examples of the base X include DBU, piperidine, DBN, MTBD, pyrrolidine, morpholine, 1,1,3,3-tetramethylguanidine, and TBD, with DBU or piperidine being preferred, and with DBU being most preferred among these. In some embodiments, the base X may be a non-nucleophilic base.

The term "pKa" as used herein can be measured using water as a solvent. Observed values previously reported as pKa in case of using water as a solvent may be employed as pKa as used herein. When observed pKa values are not available, values calculated using ADMETPredictor (Simulations Plus Inc., ver. 8.0) may be employed as pKa as used herein. pKa of representative reagents are listed as follows:

The conjugate acid of DBU (pKa=11.9; R. Srivastava, J. Mol. Catal. A: Chem. 264 (2007) 146-152);

The conjugate acid of piperidine (pKa=11.22; Hall, H. K., Jr. J. A.m. Chem. Soc. 1957, 79, 5441);

The conjugate acid of $Et_3N$ (pKa=10.65; Hall, H. K., Jr. J. A.m. Chem. Soc. 1957, 79, 5441);

The conjugate acid of DIPEA (pKa=11.44; Chemical and Pharmaceutical Bulletin, 1995, 43, 1872-1877);

The conjugate acid of 2,4,6-trimethylpyridine (pKa=7.48; Clarke, K., Rothwell, K. J. Chem. Soc. 1960, 1885);

The conjugate acid of 2,6-dimethylpyridine (pKa=6.77; Clarke, K., Rothwell, K. J. Chem. Soc. 1960, 1885);

The conjugate acid of pyridine (pKa=5.21; D. H. Ripin, D. A. Evans, pKa's of Nitrogen Acids, [online], [retrieved on Dec. 5, 2017], internet <URL:

http:_evans.rc.fas.harvard.edu/pdf/evans_pKa_table pdf>);
  TsOH (pKa = −6.62; J. Org. Chem., 1986, 51, 5013-5015);
  HOAt (pKa = 3.28; Chem. Eur. J. 2009, 15, 9394-9403);
  HOBt (pKa = 4.60; Chem. Eur. J. 2009, 15, 9394-9403);
  oxyma (pKa = 4.60; Chem. Eur. J. 2009, 15, 9394-9403);
  HCl (pKa = −8.0; D.H. Ripin, D.A. Evans, pKa's of Inorganic and Oxo-Acids, [online],
    [retrieved on December 5, 2017], internet <URL: http://evans.rc.fas.
    harvard.edu/pdf/evans_pKa_table.pdf>);
  HFIP (pKa = 9.3; Tetrahedron Asymmetry, 2012, 23, 1023-1027).

The pKa of conjugate acids of the N-terminal amino groups of amino group-containing compounds may be regarded as the pKa of conjugate acids of the N-terminal amino groups of the amino acid residues located at the N-terminus. The values observed for compounds simulating the amino acid residues located at the N-terminus may be employed as such pKa. Alternatively, the pKa may be measured or calculated using the same compound. Examples of the compounds simulating the amino acid residues located on the N-terminus include the following compounds, along with examples of the pKa of the conjugate acids of their amino groups (values calculated by ADMETPredictor (Simulations Plus Inc., ver. 8.0)): the conjugate acid of H-MeGly-NHMe (pKa=8.62); the conjugate acid of H-MeGly-NMe2 (pKa=8.63); the conjugate acid of H-MeAla-NHMe (pKa=8.69); the conjugate acid of H-MeAla-NMe2 (pKa=8.68); the conjugate acid of H-Ala-NHMe (pKa=8.47); the conjugate acid of H-MePhe-NHMe (pKa=8.16); the conjugate acid of H-Phe-NHMe (pKa=7.78); the conjugate acid of H-MeVal-NHMe (pKa=8.75); the conjugate acid of H-Val-NHMe (pKa=8.27); and the conjugate acid of H-MeAla-D-3-MeAbu-(O-2-Cl-Trt) (pKa=8.33).

In some embodiments, a salt of the present disclosure may be a salt formed of a base Y and an acid Z. As a method of preparing a composition comprising a salt of the present disclosure, a salt may be dissolved in a solvent, or both a base and an acid may be added to a solvent to form a salt in solution. Examples of the solvents for dissolving a salt or for dissolving a base and an acid include, but are not particularly limited to, dichloromethane, DMF, NMP, THF, and acetonitrile.

In some embodiments, the pKa of a conjugate acid of a base Y of the present disclosure may be smaller than the pKa of a conjugate acid of a base X by, for example, 0.3 or more, 0.5 or more, or 1.0 or more as a pKa value. In some embodiments, selection of such a base Y allows a salt of the present disclosure to inactivate a base X. Without being intended to be bound to any particular theory, it is considered that selection of such a base Y allows a proton to transfer from a salt of the present disclosure to a base X and allows an acid Z constituting the salt to newly form a salt with the base X, so that the base X can be inactivated. In this manner, the base X can be inactivated by making the pKa of the conjugate acid of the base Y smaller than the pKa of the conjugate acid of the base X. Therefore, those skilled in the art will naturally understand that if this condition of pKa is satisfied, the effect of inactivating the base X can be exerted irrespective of the type of the base Y of the present disclosure.

In some embodiments, the conjugate acid of the base Y of the present disclosure may have a pKa of 15.0 or less, 13.5 or less, 12.5 or less, 11.5 or less, or 11.0 or less.

In some embodiments, the base Y of the present disclosure may be a base, a conjugate acid of which has a pKa of 5.0 or more, 5.5 or more, 6.0 or more, 6.5 or more, 7.0 or more, 8.0 or more, 9.0 or more, 10.0 or more, or 10.5 or more. In some embodiments, the base Y may be selected to form a salt with the acid Z, and the pKa of a conjugate acid of the base Y may be larger than the pKa of the acid Z. In some embodiment, the base Y of the present disclosure may be a base, a conjugate acid of which has a pKa larger than that of conjugate acids of the N-terminal amino groups of amino group-containing compounds. The amino group-containing compounds may be the amino group-containing compounds in step (a) of the present disclosure. Without being intended to be bound by any particular theory, it is considered that if the pKa of the conjugate acid of the base Y is larger than the pKa of the conjugate acids of the N-terminal amino groups of the amino group-containing compounds, reduced elongation reactivity due to protonation of the N-terminus can be avoided and the peptide elongation reaction proceeds more efficiently. However, even if the pKa of the conjugate acid of the base Y is smaller than the pKa of the conjugate acids of the N-terminal amino groups of the amino group-containing compounds, redundant peptide elongation can be suppressed and washing frequency and an amount of the washing solution can be reduced. Such an embodiment is also included in an embodiment of the present disclosure.

In some embodiments, the base Y of the present disclosure is a base different in type from the base X. In some embodiments, the base Y may be an organic base, particular examples of which include amines and pyridines. More specific examples of the base Y include triethylamine (Et3N), N,N-diisopropylethylamine (DIPEA), trimethylamine, tributylamine, pyridine, 2,6-dimethylpyridine (2,6-lutidine), 2,4,6-trimethylpyridine (2,4,6-collidine), and derivatives thereof, preferably Et3N, DIPEA, 2,4,6-trimethylpyridine, and derivatives thereof, and more preferably Et3N and DIPEA.

In some embodiments, the acid Z of the present disclosure may be an acid that can inactivate the base X. The acid Z can be appropriately selected according to the base X. Examples include acids having a pKa of 5.0 or less, 4.8 or less, 4.5 or less, 4.0 or less, or 3.0 or less. In some embodiments, the lower limit of the pKa of the acid Z of the present disclosure is not particularly limited, provided that the acid Z can inactivate the base X. Examples of the acid Z include acids having a pKa of −10.0 or more, −9.0 or more, or −8.0 or more. In some embodiments, the acid Z may be selected to form a salt with the base Y, and the pKa of the acid Z may be smaller than the pKa of the conjugate acid of the base Y. Examples of the acid Z of the present disclosure include hydrochloric acid, HOAt, HOBt, oxyma, HOOBt, and sulfonic acid (such as TsOH).

In some embodiments, preferred combinations of the base X, the base Y, and the acid Z in the present invention include a combination selected from the group consisting of (a) to (t) in Table 2.

TABLE 2

| | Base X | Base Y | Acid Z |
|---|---|---|---|
| (a) | DBU | Et3N | HCl |
| (b) | DBU | Et3N | TsOH |
| (c) | DBU | Et3N | HOAt |
| (d) | DBU | Et3N | HOBt |
| (e) | DBU | Et3N | oxyma |
| (f) | DBU | DIPEA | HCl |
| (g) | DBU | DIPEA | TsOH |
| (h) | DBU | DIPEA | HOAt |
| (i) | DBU | DIPEA | HOBt |
| (j) | DBU | DIPEA | oxyma |
| (k) | DBU | 2,4,6-Collidine | HCl |
| (l) | DBU | 2,4,6-Collidine | TsOH |
| (m) | DBU | 2,4,6-Collidine | HOAt |
| (n) | DBU | 2,4,6-Collidine | HOBt |
| (o) | DBU | 2,4,6-Collidine | oxyma |
| (p) | DBU | Pyridine | HCl |
| (q) | DBU | Pyridine | TsOH |
| (r) | DBU | Pyridine | HOAt |
| (s) | DBU | Pyridine | HOBt |
| (t) | DBU | Pyridine | oxyma |

As used herein, the term "inactivation" refers to reduction or elimination of inherently possessed activity. Inactivation as used herein includes inactivation of deprotection activity. For example, when a base is used as a deprotecting agent, inactivation of the base refers to reduction or elimination of deprotection activity inherently possessed by the base. The degree of reduction in this context may be exemplified by, but is not limited to, 80% or more, 85% or more, 90% or more, 95% or more, 97% or more, 98% or more, or 99% or more. Inactivation of a base as used herein includes neutralization of the base. As used herein, deprotection activity refers to activity to remove a certain protecting group for a functional group. Reduction of activity is not particularly limited if the activity is reduced to the extent that it does not affect the desired reaction. In some embodiments, inactivation of a base may be confirmed by a rate of production of redundantly elongated peptides reduced to 2% or less, 1% or less, 0.5% or less, 0.1% or less, or 0.05% or less when peptide elongation reaction is conducted according to the method described in Examples.

In some embodiments, the deprotecting agents can be selected according to the type of the protecting groups to be used. Examples of the deprotecting agents for protecting groups having an Fmoc backbone include bases (such as DBU and piperidine). Examples of the deprotecting agents for Boc, tBu, Trt, THP, or the like include acids (such as TFA). Examples of the deprotecting agents for a benzyloxycarbonyl group (Cbz) or the like include transition metal catalysts (such as Pd/C) in the coexistence with hydrogen. Examples of the deprotecting agents for allyl, Alloc, or the like include palladium catalysts (such as a combination of PhSiH3 and Pd(PPh3)4) in the coexistence with a reducing agent or a nucleophile. Examples of the deprotecting agents for Dde or ivDde include hydrazine. Examples of the deprotecting agents for o-NBS include thiols (such as a combination of DBU and 1-dodecanethiol) in the presence of a base. The examples are not limited to the above.

In some embodiments, a method of producing a peptide and/or a method of treating a base X in the production of a peptide of the present disclosure (also called "the methods of the present disclosure") may include at least one step selected from the group consisting of the following steps (a'), (a), and (b):

(a') removing with a base X a protecting group Q of an amino group-containing compound protected by the protecting group Q;

(a) allowing the base X, the amino group-containing compound, and a salt formed of a base Y and an acid Z to coexist; and
(b) after the step (a), allowing the amino group-containing compound and an amino acid or peptide having an amino group protected by a protecting group P to coexist to elongate a peptide chain.

Step (b) of the present disclosure may also be rephrased as a step of forming an amide bond between the amino group-containing compound and an amino acid having an amino group protected by a protecting group P or a peptide having an amino group protected by a protecting group P (this peptide may be called "peptide 1") to obtain a "peptide 2". The term "peptide 2" of the present disclosure may be a peptide obtained by linking the amino group-containing compound to an amino acid having an amino group protected by a protecting group P through an amide bond, or a peptide obtained by linking the amino group-containing compound to a "peptide 1" through an amide bond, and is a peptide to be produced in the present disclosure.

The methods of the present disclosure may also be described as follows:

A method of producing an elongated amino group-containing compound, the method comprising at least one step selected from the group consisting of the following steps (a'), (a), and (b):
(a') removing with a base X a protecting group Q of an amino group-containing compound protected by the protecting group Q;
(a) allowing the base X, the amino group-containing compound, and a salt formed of a base Y and an acid Z to coexist; and
(b) after the step (a), allowing the amino group-containing compound and an amino acid having an amino group protected by a protecting group P or a peptide having an amino group protected by a protecting group P to coexist and linking the compound to the amino acid having an amino group protected by a protecting group P or the peptide having an amino group protected by a protecting group P, thereby obtaining an elongated amino group-containing compound.

Alternatively, the methods of the present disclosure relate to a method of elongating an amino group-containing compound, the method comprising at least one of the above steps.

Alternatively, the methods of the present disclosure may be described as follows:

A method of treating a base X in the production of an elongated amino group-containing compound, the method comprising at least one step selected from the group consisting of the following steps (a'), (a), and (b):
(a') removing with a base X a protecting group Q of an amino group-containing compound protected by the protecting group Q;
(a) allowing the base X, the amino group-containing compound, and a salt formed of a base Y and an acid Z to coexist; and
(b) after the step (a), allowing the amino group-containing compound and an amino acid having an amino group protected by a protecting group P or a peptide having an amino group protected by a protecting group P to coexist and link the compound to the amino acid having an amino group protected by a protecting group P or the peptide having an amino group protected by a protecting group P, thereby obtaining an elongated amino group-containing compound.

Alternatively, the methods of the present disclosure relate to a method of treating a base X in the elongation of an amino group-containing compound, the method comprising at least one of the above steps.

In some embodiments, a method of producing a peptide or a method of treating a base X in the production of a peptide of the present disclosure may include (1) steps (a) and (b) above; (2) steps (a'), (a), and (b) above; or (3) steps (a') and (a) above. In some embodiments, step (a') is performed prior to step (a).

Step of Providing an Amino Group-Containing Compound Protected by a Protecting Group Q An amino group-containing compound protected by a protecting group Q, which is used in step (a'), can be provided, for example, by the following methods. An example thereof is a method of attaching a compound (such as an amino acid or peptide) having an amino group protected by a protecting group Q to a solid-phase support. In some embodiments, such method is, but is not limited to, a method of attaching the carboxy group of a compound having an amino group protected by a protecting group having an Fmoc backbone to a solid-phase support having a trityl group. In this manner, an amino group-containing compound protected by a protecting group Q can be provided using a method well-known in the art. As another method, functional groups other than the amino group protected by a protecting group Q may be protected by other protecting groups to provide the target compound. In this case, the protecting groups other than the protecting group Q are preferably protecting groups that cannot be removed with a base. This procedure can be performed, for example, according to the method described in WO 2013/100132.

Step (a'): Step of Removing the Protecting Group

Step (a') may be performed under conditions where the protecting group Q is removed, and an organic solvent may be used as a solvent. Examples of such organic solvents include, but are not particularly limited to, DMF and NMP, and they may be used in combination as appropriate. When DBU is used, for example, as the base X, this step may be performed by treatment with a solution containing 2% (by volume) of DBU in a solvent such as DMF. In this case, the step may be performed, for example, by shaking at room temperature for 10 min. When piperidine is used, for example, as the base X, this step may be performed by treatment with a solution containing 10-50% (by volume) of piperidine in a solvent such as NMP or DMF. In some embodiments, the amino group-containing compound in step (a) can be produced in this step.

The amino group-containing compound protected by a protecting group Q, which is used in this step, may be an amino acid or peptide, each having an amino group protected by a protecting group Q. In this case, the amino acid or peptide may be attached to a solid-phase support or have a carboxy group protected by a protecting group. The solid-phase support, or the protecting group for the carboxy group, is preferably one that is hardly cleavable or removable under conditions for deprotection of the amino group protected by the protecting group Q, and is preferably one that can be cleaved or removed with an acid.

Step (a): Step of Allowing Coexistence of a Salt

Step (a) may be performed by a method that can allow coexistence of the base X, the amino group-containing compound, and a salt formed of a base Y and an acid Z, and is not particularly limited. In some embodiments, a base Y may be previously mixed with an acid Z to form a salt. In other embodiments, a base Y and an acid Z may be separately mixed into a solvent to form a salt in the solvent. In some embodiments, step (a) may be performed by mixing the base X, the amino group-containing compound, and a salt formed of a base Y and an acid Z. In some embodiments, step (a) may be performed by mixing the base X, the amino group-containing compound, a base Y, and an acid Z. In some embodiments, step (a) may be performed by mixing a mixture comprising the base X and the amino group-containing compound with a salt formed of a base Y and an acid Z or a composition comprising such a salt. In other embodiments, step (a) may be performed by mixing a mixture comprising the base X and the amino group-containing compound with a base Y and an acid Z (or a composition comprising a base Y and a composition comprising an acid Z). The compositions may each be a solution. The order of mixing the components is not particularly limited. The base X in step (a) may be the remainder of the base X used in step (a'). Examples of the solvents used in step (a) include, but are not particularly limited to, DCM, DMF, and NMP, and they may be used in combination as appropriate. In some embodiments, after step (a), the next step may be performed following removal of the solvent used in the step (a), or step (a) may be repeated. In some embodiments, step (a) may be a step to inactivate the base X. The amount of the salt added in this step (a) is not particularly limited, but is preferably larger than the amount of the remaining base X (number of moles). In this case, the remaining amount may be the amount obtained by subtracting the amount of the base X eliminated after deprotection from the amount of the base X used for deprotection. The amount of the eliminated base X may be determined using an analytical instrument such as NMR, LC, or GC. The time of treatment with a salt is not particularly limited, and may be, for example, 5 minutes to 15 minutes. Step (a) may be performed to inactivate the base X.

Step (b): Step of Elongating a Peptide Chain

In some embodiments, this step may be performed by mixing a mixture comprising the amino group-containing compound with an amino acid or peptide having an amino group protected by a protecting group P. In some embodiments, this step may be performed under conditions where a peptide chain is elongated. In some embodiments, the amino acid or peptide having an amino group protected by a protecting group P, which is used in this step, may be an amino acid or peptide having a carboxy group that is free or converted to an active ester, preferred examples of which include amino acids or peptides having one carboxy group that is free or converted to an active ester. In some embodiments where the amino acid or peptide having an amino group protected by a protecting group P has a free carboxy group, the carboxy group may be converted to an active ester in the same reaction system as that for peptide elongation in step (b).

As a method of converting the carboxy group possessed by the amino acid or peptide used in this step to an active ester, a method well-known in the art may be used, an example of which is a method of forming an active ester by allowing a carbodiimide-type condensing agent represented by DIC and a highly nucleophilic reagent (such as HOBt, HOAt, HOSu, Oxyma, or HOOBt) to coexist. The conversion to an active ester may be previously performed before step (b), or may be performed in step (b).

Peptide chain elongation in this step may be performed in the presence of a condensing agent. In some embodiments, peptide chain elongation in this step may be performed through an amide bond formation. In this case, a condensing agent and an amount of use thereof for condensing an amino group with a carboxy group are not particularly limited, provided that an amide bond can be formed, and are preferably a condensing agents and an amount of use thereof which are generally used in peptide synthesis (e.g., Peptide Coupling Reagents, More than a Letter Soup (Chem. Rev. 2011, 111, 6557-6602)). Specific examples of such condensing agents include condensing agents having a carbodiimide backbone. For example, such condensing agents having a carbodiimide backbone can be used in condensation reaction in combination with a hydroxy compound that can form an active ester. Examples of the condensing agents having a carbodiimide backbone include N,N'-dicyclohexylcarbodiimide (DCC), N,N'-diisopropylcarbodiimide (DIC), and 1-ethyl-3-(3-dimethylaminopropyl)carbodiimide hydrochloride (WSCI.HCl) (see e.g., a catalog of WATANABE Chemical, Amino acids and chiral building blocks to new medicine). Examples of the hydroxy compounds that can form an active ester include 1-hydroxy-1H-benzotriazole (HOBt), 1-hydroxy-7-azabenzotriazole (HOAt), ethyl 2-cyano-2-(hydroxyimino)acetate (oxyma), 3,4-dihydro-3-hydroxy-4-oxo-1,2,3-benzotriazine (HOOBt or HODhbt), N-hydroxy-5-norbornene-2,3-dicarboximide (HONB), 2,3,4,5,6-pentafluorophenol (HOPfp), N-hydroxysuccinimide (HOSu), and 6-chloro-1-hydroxy-1H-benzotriazole (Cl-HOBt) (see e.g., a catalog of WATANABE Chemical, Amino acids and chiral building blocks to new medicine). Salts having such a backbone can also be used, such as a potassium salt of oxyma, K-oxyma. Among them, HOBt, HOAt, oxyma, and HOOBt are particularly preferred. In particular, a combination of DIC and HOAt or a combination of DIC and oxyma is preferably used. In addition, any of phosphonium-type or uronium-type condensing agents may be utilized including O-(1H-benzotriazol-1-yl)-N,N,N',N'-tetramethyluronium hexafluorophosphate (HBTU), O-(7-aza-1H-benzotriazol-1-yl)-N,N,N',N'-tetramethyluronium hexafluorophosphate (HATU), N-[1-(cyano-2-ethoxy-2-oxoethylidenaminooxy)dimethylamino(morpholino)]uronium hexafluorophosphate (COMU), O-[(ethoxycarbonyl)cyanomethyleneamino]-N,N,N',N'-tetramethyluronium hexafluorophosphate (HOTU), O-(1H-benzotriazol-1-yl)-N,N,N',N'-tetramethyluronium tetrafluoroborate (TBTU), O-(7-azabenzotriazol-1-yl)-N,N,N',N'-tetramethyluronium tetrafluoroborate (TATU), 1H-benzotriazol-1-yloxy-tri(pyrrolidino)phosphonium hexafluorophosphate (PyBOP), 1H-benzotriazol-1-yloxy-tris(dimethylamino)phosphonium hexafluorophosphate (BOP), bromotri(pyrrolidino)phosphonium hexafluorophosphate (PyBroP), chlorotri(pyrrolidino)phosphonium hexafluorophosphate (PyCloP), (7-azabenzotriazol-1-yloxy)tripyrrolidinophosphonium hexafluorophosphate (PyAOP), bromotris(dimethylamino)phosphonium hexafluorophosphate (Brop), 3-(diethoxyphosphoryloxy)-1,2,3-benzotriazin-4(3H)-one (DEPBT), N,N,N',N'-tetramethyl-O—(N-succinimidyOuronium tetrafluoroborate (TSTU), N,N,N',N'-tetramethyl-O—(N-succinimidyOuronium hexafluorophosphate (HSTU), O-(3,4-dihydro-4-oxo-1,2,3-benzotriazin-3-yl)-N,N,N',N'-tetramethyluronium tetrafluoroborate (TDBTU), tetramethylthiuronium S-(1-oxido-2-pyridyl)-N,N,N',N'-tetrafluoroborate (TOTT), and O-(2-oxo-1(2H)-pyridyl)-N,N,N',N'-tetramethyluronium tetrafluoroborate (TPTU) in condensation reaction in combination with any of bases including N,N-diisopropylethylamine (DIPEA), triethylamine (TEA), 2,4,6-trimethylpyridine (2,4,6-collidine), and 2,6-dimethylpyridine (2,6-lutidine). In particular, a combination of HATU and DIPEA or a combination of COMU and DIPEA is preferably used. In addition, condensing agents such as N,N'-carbonyldiimidazole (CDI), 1,1'-carbonyl-di-(1,2,4-triazole) (CDT), 4-(4,6-dimethoxy-1,3,5-triazin-2- yl)-4-methylmorpholinium chloride (DMT-MM), and propylphosphonic anhydride (T3P) can also be used. Examples of solvents used in this step include, but are not particularly limited to, NMP, DMF, THF, and acetonitrile, and they may be used in combination as appropriate.

The amount of the amino group-protected amino acid or peptide used in this step is preferably an equivalent amount or more (one equivalent or more), and more preferably 1.5 equivalents or more relative to the amount of the amino group-containing compound prepared as a starting material for peptide production. Examples of the starting materials for peptide production as used herein include an amino group-containing compound attached to a solid-phase support and an amino group-containing compound having a carboxy group protected by a protecting group.

The completion of this step can be monitored by a quantitative ninhydrin test. After the condensation reaction is determined to be completed, the condensation reaction mixture may be washed with a solvent and the condensation reaction may be repeated for each subsequent amino acid residue of peptides.

The methods of the present disclosure may be a method in which the above steps (a') to (b) (which means steps (a'), (a), and (b) are conducted in this order) are repeated twice or more, three times or more, or four times or more. A peptide chain can be elongated by such a repetition. Specifically, when steps (a') to (b) are repeated, for example, twice, a compound whose peptide chain is elongated in the first-round step (b) becomes the "amino group-containing compound protected by a protecting group Q" in the second-round step (a'). When steps (a') to (b) are repeated multiple times, the protecting group Q, protecting group P, base X, base Y, or acid Z used in each cycle may be independently of the same or different type.

The methods of the present disclosure may further comprise, after the step (b), either or both of the following steps of:
(c1) cleaving a peptide from the solid-phase support; and
(c2) removing the protecting groups of the peptide.

Step (c1): Step of Cleavage from the Solid-Phase Support

This step is a step of cleaving elongated peptides from the solid-phase support after the final round step (b) is conducted. The peptides may also be structurally transformed or cyclized before the cleaving step. In some embodiments, at the time of cleavage, side chain functional groups protected by protecting groups may or may not be deprotected, or only some of the protecting groups may be deprotected. The cleaving step is preferably conducted with the side chain functional groups being protected. Retainment of protecting groups in this manner can prevent undesired coupling of peptide fragments or other undesired reactions. When the peptides are modified (e.g., derivatized or cyclized) after this step, only the protecting groups for the functional groups necessary for the subsequent reaction may be removed.

In some embodiments, the peptides may be cleaved from the solid-phase support by washing the solid-phase support with a solvent such as DMF or DCM and then treating it with a solution containing 50 v/v % of TFE in a solvent such as DCM. The cleaving method is not particularly limited and can be selected according to the type of the solid-phase support. When the peptides are synthesized using the Fmoc strategy or a similar chemical synthesis method, protecting groups may be removed in any manner, and may be removed, for example, using a relatively weak acid such as acetic acid or diluted TFA in a solvent such as DCM. Typically, 0.5 to 10 vol %, and preferably 1 to 3 vol %, of TFA may be used in DCM.

After cleaving the peptides from the solid-phase support, a compound in an amount sufficient to quench the cleaving reaction may be added to cleaved peptide compositions. For example, in some embodiments, pyridine (a quenching compound) may be added to the compositions in an amount about twice the amount of TFA added in the above-described cleaving step. Next, the peptide products may be concentrated in a solvent and extracted with an aqueous liquid.

Step (c2): Step of Removing the Protecting Groups of the Peptide

This step is a step of removing the protecting groups of the elongated peptides after the final round step (b) is conducted. In some embodiments, the protecting groups may be removed by washing the peptides with a solvent such as DMF, NMP, or dichloromethane and then treating it with a solution containing 20% of piperidine or 2% of DBU in a solvent such as DMF or NMP. The method of removing the protecting groups is not particularly limited and can be selected according to the type of the protecting groups to be removed. The protecting groups for the functional groups in the peptides may be removed all at the same time or may be removed separately. When the peptides are modified (e.g., derivatized or cyclized) after this step, only the protecting groups for the functional groups necessary for the subsequent reaction may be removed.

The above-described steps may be conducted consecutively, or an optional step may be included between the above-described steps. An example of such an optional step is a washing step. Washing may also be performed simultaneously with step (a).

Washing Step

In some embodiments, the methods of the present disclosure may include a washing step between the steps (a') and (b). The methods may also include a washing step between the steps (b) and (c1) or between the steps (b) and (c2). An example of such washing is washing of the solid-phase support. Substances unnecessary for the peptide chain elongation reaction in step (b) (such as by-products, bases, or salts) can be removed by conducting washing between steps (a') and (a) and/or between steps (a) and (b). The remainder of reagents used for peptide chain elongation or by-products can be removed by conducting washing between steps (b) and (c1) or between steps (b) and (c2).

In some embodiments, the methods of the present disclosure do not have to include a washing step or may include an arbitrary number of times of washing steps (for example, though not particularly limited to, once to five times or once to three times) between steps (a) and (b). In some embodiments, the methods do not have to include a washing step or may include an arbitrary number of times of washing steps (for example, though not particularly limited to, once to five times in total or once to three times in total) between steps (a) and (b) and between steps (a') and (a).

A washing method used in the washing step of the present disclosure is not particularly limited, and washing solvent, washing frequency, treating time, and the like can be appropriately selected depending on the purpose. The washing solvent to be used is not particularly limited, and may be an organic solvent, examples of which include DCM, DMF, NMP, THF, acetonitrile, isopropyl alcohol, and a combination of two or more selected therefrom. Washing may also be performed simultaneously with step (a) of the present disclosure by using a washing solvent containing a salt of the present disclosure (a salt formed of a base Y and an acid Z). In the present specification, such a washing method may be called "salt washing" or "salt washing method".

In some embodiments of the methods of the present disclosure, washing frequency can be reduced. A manual from Bachem A G for a method of producing a peptide (Solid Phase Peptide Synthesis, 2016; table 10) discloses a method in which washing is conducted nine times between steps (a') and (b). According to some embodiments of the methods of the present disclosure, when washing is conducted between steps (a') and (b) and simultaneously with step (a) (for example, in the case of conducting salt washing), undesirable side reactions can be suppressed by conducting, in addition to the above washing, once, twice, three times, four times, or five times of washing. Specifically, a washing step may be included between the steps (a) and (b), and the washing frequency in the step can be exemplified by once, twice, three times, four times, or five times. Even if the washing frequency similar to that used in a conventional peptide production method is employed, use of the methods of the present disclosure can produce a strong effect of suppressing redundant elongation and a target peptide in a high purity. The methods may or do not have to include a washing step between the steps (a') and (a).

The methods of the present disclosure may employ any peptide synthesis method irrespective of its type such as solid-phase synthesis, liquid-phase synthesis, or anchoring, but the peptide production of the present disclosure is preferably performed by solid-phase synthesis.

In some embodiments, the present disclosure provides peptides produced by the production methods of the present disclosure.

In some embodiments, high-purity target peptides can be obtained using the methods of the present disclosure. For example, target peptides can be obtained in a purity of 95% or more, 97% or more, 98% or more, 99% or more, or 99.5% or more as analyzed by LC/MS according to the method described in Examples.

In some embodiments, the peptides produced by the methods of the present disclosure may be peptides having two or more amide bonds. In some embodiments, the peptide production methods of the present disclosure may be methods of producing peptides having two or more, three or more, or four or more amide bonds. In some embodiments, the peptide production methods of the present disclosure may be methods of producing peptides in which three or more, or four or more, amino acids are sequentially linked through amide bonds.

In some embodiments, the peptides produced by the methods of the present disclosure may be peptides containing at least one, or two or more, or three or more N-substituted amino acids. Examples of the N-substituted amino acids include N-alkylamino acids, preferably N-alkyl (C1-6) amino acids and N-alkyl (C1-3) amino acids, and more preferably N-methylamino acids. As used herein, a peptide containing a certain amino acid may refer to a peptide containing such an amino acid residue.

In some embodiments, the peptides produced by the methods of the present disclosure may be peptides where the number of amino acids is 2 to 50, examples of which include peptides where the number of amino acids is 2 to 30, 2 to 20, and 2 to 15.

In some embodiments, a cyclic peptide can be produced by the methods of the present disclosure. The methods of the present disclosure can produce peptides which contain on the C-terminal side an amino acid residue having one reaction point on the side chain and contain on the N-terminal side an amino acid residue having another reaction point. Such peptides can be produced by selecting raw materials such that the peptides contain on the C-terminal side an amino acid residue having one reaction point on the side chain and contain on the N-terminal side an amino acid residue having another reaction point. The peptides can then be cyclized by attaching the one reaction point to the other reaction point. In this manner, the methods of the present disclosure may include the cyclization step described above. An illustrative cyclization method is described in WO 2013/100132.

In some embodiments, the present disclosure provides inactivating agents for a base X for use in the methods of the present disclosure. The inactivating agents may contain a salt formed of a base Y and an acid Z.

In some embodiments, the inactivating agents of the present disclosure may be mixed with a solvent. As a method of preparing the inactivating agents of the present disclosure, for example, a salt may be dissolved in the above-described solvent or both a base and an acid may be added individually to the solvent to form a salt in a solution. A salt may also be formed in a solution by mixing a composition comprising a base with a composition comprising an acid. Examples of the solvents for dissolving a salt or for dissolving a base and an acid include, but are not particularly limited to, DCM, DMF, and NMP.

EXAMPLES

The present invention will be further illustrated by the following Examples, but is not limited thereto.

Reagents whose synthesis or preparation method is not particularly described in the Examples were purchased as commercially available products from companies such as Wako Pure Chemical Industries, Ltd., Tokyo Chemical Industry Co., Ltd., and Aldrich. As reaction solvents used for peptide synthesis and solid-phase synthesis, those for use in peptide synthesis were used (purchased from Watanabe Chemical Industries, Ltd. and Wako Pure Chemical Industries, Ltd.). Examples thereof include DCM, DMF, NMP, 2% DBU in DMF, and 20% piperidine in DMF. Dehydrated solvents, ultradehydrated solvents, and anhydrous solvents (purchased from Kanto Chemical Co., Inc., Wako Pure Chemical Industries, Ltd., and others) were used for reactions in which water was not added as a solvent. In the Examples, solid-phase supports may be called resins.

The LCMS analysis conditions are as described in Table 3.

TABLE 3

| Analysis condition | Instrument | Column (I.D. × length) (mm) | Mobile phase | Gradient (A/B) | Flow rate (mL/min) | Column temperature (° C.) | Wavelength |
|---|---|---|---|---|---|---|---|
| SQDFA05 | Acquity UPLC/SQD2 | Ascentis Express C18 (2.1 × 50) | A) 0.1% FA, H$_2$O B) 0.1% FA, MeCN | 95/5 = >0/100 (1.0 mm) 0/100 (0.4 min) | 1 | 35 | 210-400 nm PDA total |
| SQDFA50 | Acquity UPLC/SQD2 | Ascentis Express C18 (2.1 × 50) | A) 0.1% FA, H$_2$O B) 0.1% FA, MeCN | 50/50 = >0/100 (0.7 min) 0/100 (0.7 min) | 1 | 35 | 210-400 nm PDA total |

Example 1: Preparation of Salts Formed of Bases and Acids

Example 1-1: Preparation of Diisopropylethylamine Hydrochloride (Compound 1, DIPEA.HCl)

Chemical formula 2

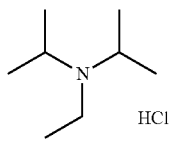

Dichloromethane (20 mL) was added to diisopropylethylamine (5.0 g, 6.8 mL), and a 4 N hydrochloric acid/1,4-dioxane solution (19.3 mL) was added dropwise under ice-cooling. The mixture was stirred under ice-cooling for 10 min, and the solvent was then removed by evaporation under reduced pressure. The resulting residue was further dried under reduced pressure at room temperature to give the title Compound 1 (6.4 g).

$^1$H NMR (BRUKER Ascend 400, 400 MHz, DMSO-d6) δ 10.020 (1H, bs), 3.626-3.551 (2H, m), 3.141-3.076 (2H, m), 1.339-1.276 (15H, m)

Example 1-2: Preparation of Diisopropylethylamine p-Toluenesulfonate (Compound 2, DIPEA.TsOH)

Chemical formula 3

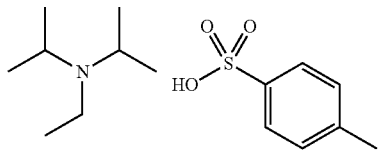

Dichloromethane (20 mL) was added to TsOH.H$_2$O (5.9 g), and diisopropylethylamine (5.0 g, 6.8 mL) was added dropwise under ice-cooling. The mixture was stirred under ice-cooling for 10 min, and the solvent was then removed by evaporation under reduced pressure. The resulting residue was further dried under reduced pressure at room temperature to give the title Compound 2 (9.3 g).

$^1$H NMR (BRUKER Ascend 400, 400 MHz, DMSO-d6) δ 8.227 (1H, bs), 7.485 (2H, d, J=8.0), 7.121 (2H, d, J=8.0), 3.618-3.589 (2H, m), 3.131-3.114 (2H, m), 2.289 (3H, s), 1.263-1.192 (15H, m)

Example 1-3: Preparation of (Compound 3, DIPEA.HOAt)

Chemical formula 4

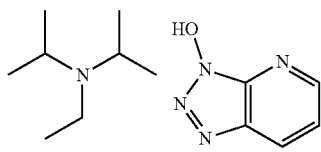

The title Compound 3 (8.2 g) was obtained according to the method described in Example 1-2, except that HOAt (4.2 g) was used instead of TsOH.H$_2$O (5.9 g).

$^1$H NMR (BRUKER Ascend 400, 400 MHz, DMSO-d6) δ 10.601 (1H, bs), 8.368 (1H, dd, J=4.4, 1.2), 8.192 (1H, dd, J=8.0, 1.6), 7.209 (1H, dd, J=8.0, 4.4), 3.479 (2H, bs), 2.970 (2H, bs), 1.210-1.149 (15H, m)

Example 1-4: Preparation of (Compound 4, DIPEA.Oxyma)

Chemical formula 5

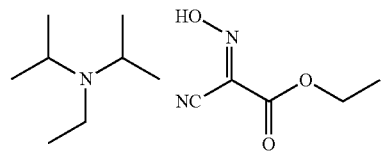

The title Compound 4 (8.2 g) was obtained according to the method described in Example 1-2, except that oxyma (4.4 g) was used instead of TsOH.H$_2$O (5.9 g).

$^1$H NMR (BRUKER Ascend 400, 400 MHz, DMSO-d6) δ 8.530 (1H, bs), 4.192 (2H, q, J=6.8), 3.600-3.568 (2H, m), 3.110-3.093 (2H, m), 1.261-1.210 (18H, m)

Example 1-5: Preparation of (Compound 5, DIPEA.HOBt)

Chemical formula 6

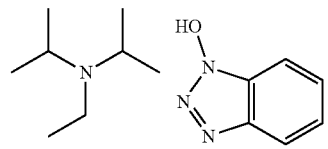

The title Compound 5 (8.3 g) was obtained according to the method described in Example 1-2, except that HOBt (4.7 g) was used instead of TsOH.H$_2$O (5.9 g).

1H NMR (BRUKER Ascend 400, 400 MHz, DMSO-d6) δ 7.760-7.737 (1H, m), 7.447-7.426 (1H, m), 7.241-7.171 (2H, m), 3.459-3.431 (1.6H, m), 2.951-2.934 (1.6H, m), 1.186-1.139 (12H, m)

The $^1$H NMR shows that Compound 5 was obtained as a mixture containing 0.8 equivalent of DIPEA relative to HOBt (1 equivalent). In the following study, Compound 5 was used as a salt in this proportion.

Example 2: Preparation of Peptide-Loaded Solid-Phase Supports

Example 2-1: Preparation of Fmoc-Asp(O-Trt(2-Cl)-Resin)-Pip (Compound 31)

As a preparation of a peptide-loaded solid-phase support, a 2-chlorotrityl resin attached to the side chain carboxy group of aspartic acid with the N-terminus protected by Fmoc (Fmoc-Asp(O-Trt(2-Cl)-resin)-pip, (Compound 31)) was synthesized by a method described in the document (WO 2013/100132 A1).

Chemical formula 7

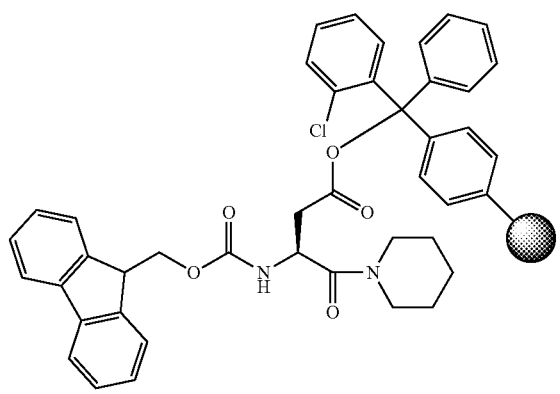

Herein, when a solid-phase support is attached to a compound, a polymer or resin moiety may be represented by "●". To clarify the point of reaction with the solid-phase support moiety, the chemical structure of a linker which is the reaction site may be shown as a structure connected to "●". For example, in the above structure (Fmoc-Asp(O-Trt (2-Cl)-resin)-pip (Compound 31)), 2-chlorotrityl group of the solid-phase support is attached to the side chain carboxy group of Asp through an ester bond. pip refers to piperidine, and the C-terminal carboxy group and piperidine form an amide bond in the above structure.

Example 2-2: Preparation of Fmoc-MePhe-MeVal-Asp(O-Trt(2-Cl)-Resin)-Pip (Compound 32) by Solid-Phase Peptide Synthesis Using an Automatic Synthesizer As an example, the prepared Fmoc-Asp(O-Trt(2-Cl)-resin)-pip (compound 31, 0.3753 mmol/g) (100 mg per column), a solution of Fmoc-MeVal-OH (0.6 mol/L) and 1-hydroxy-7-azabenzotriazole (HOAt, 0.375 mol/L) in NMP, a solution of Fmoc-MePhe-OH (0.6 mol/L) and 3,4-dihydro-3-hydroxy-4-oxo-1,2,3-benzotriazine (HOOBt, 0.375 mol/L) in NMP, and a solution of diisopropylcarbodiimide (DIC) in N,N-dimethylformamide (DMF) (10% v/v) were placed in the synthesizer.

At the start of the synthesis, 1 mL per column of dichloromethane (DCM) was added to the placed Fmoc-Asp(O-Trt(2-Cl)-resin)-pip (Compound 31) (100 mg per column), and the resin was swollen by allowing to stand for about one hour. The resin was then washed with DMF.

Deprotection Step

A solution of 1,8-diazabicyclo[5.4.0]-7-undecene (DBU) in DMF (2% v/v) was added in an amount of 0.7 mL per column, and deprotection (Fmoc removal) was conducted by allowing the mixture to stand for 5 to 10 min. The resin was then washed with DMF (0.7 mL per column, repeating four times).

Elongation Step

A solution obtained by mixing the placed Fmoc-amino acid solution (0.30 mL per column) and DIC/DMF solution (0.36 mL per column) was added to the resin that had been subjected to the deprotection step, and the resin was allowed to stand at 40° C. After the reaction was completed, the resin was washed with DMF (0.7 mL per column, four times).

In the above step, elongation with MeVal and elongation with MePhe were done in the first cycle and the second cycle, respectively. After performing elongation with MePhe, a deprotection step was not performed, and the resin Chemical formula 8

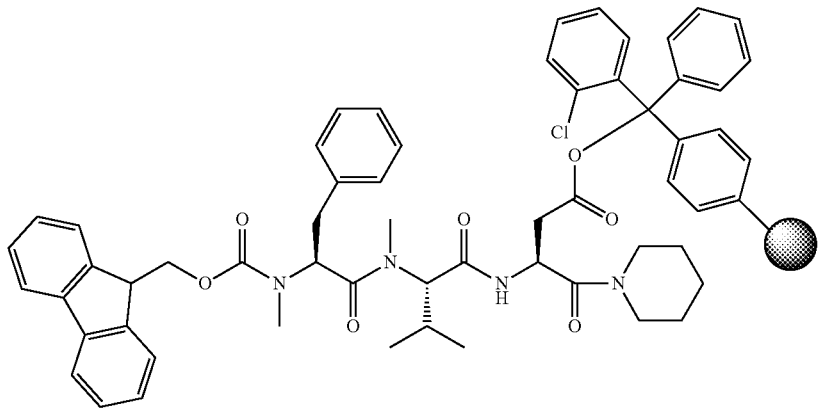

Fmoc-MePhe-MeVal-Asp(O-Trt(2-Cl)-resin)-pip (compound 32) was prepared by the Fmoc strategy using a peptide synthesizer (Multipep RS; manufactured by Intavis Bioanalytical Instruments AG). The detailed operational procedure was performed following the manual appended to the synthesizer.

was further washed with DCM, dried, and then used for a further study. To confirm that Fmoc-MePhe-MeVal-Asp(O-Trt(2-Cl)-resin)-pip (Compound 32) was prepared without any problems, a part of the resin was taken out and swollen again with DCM. The peptide was then cleaved from the resin by adding TFE/DCM (1/1, v/v), and production of the peptide (Fmoc-MePhe-MeVal-Asp-pip (Compound 50)) was confirmed by LCMS.

Cleaved Peptide (Fmoc-MePhe-MeVal-Asp-Pip (Compound 50))

Chemical formula 9

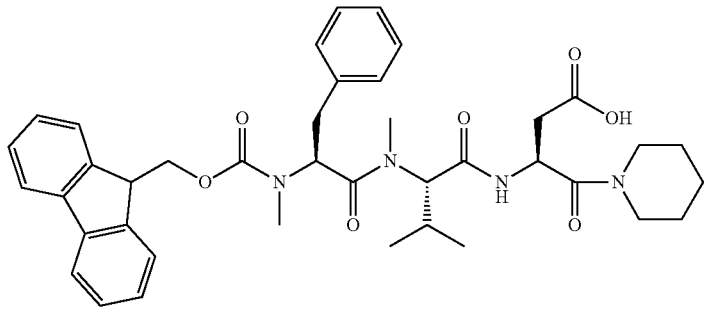

LCMS (ESI) m/z=697.4 (M+H)+
Retention time: 0.96 min (analysis condition SQDFA05)

Example 3: Suppressing Redundant Elongation by Increasing Washing Frequency

This Example was performed to confirm the effect of suppressing redundant elongation by increasing the frequency of washing the resin after Fmoc removal with a 2% DBU/DMF solution.

Example 3-1: Confirming Production of a Redundantly Elongated Peptide

This Example confirmed production of a redundantly elongated peptide in the peptide elongation using a 100 mg resin (11 area % (UV) of a redundantly elongated peptide was produced).

A 100 mg portion of the prepared Fmoc-MePhe-MeVal-Asp(O-Trt(2-Cl)-resin)-pip (Compound 32: 0.448 mmol/g) was placed in a reaction vessel equipped with a filter, and the resin was swollen by adding DCM (1 mL) and shaking the mixture at room temperature for 30 minutes. After removing the DCM with the filter, the resin was washed with DMF (1.0 mL) twice. Fmoc removal was then carried out by adding a 2% DBU/DMF solution (Fmoc removal solution: 0.7 mL) to the resin and shaking the mixture at room temperature for 30 minutes. After removing the Fmoc removal solution, the first washing was conducted by adding DMF (1 mL) and shaking the mixture at room temperature for five minutes. After removing the washing solution, the resin was further washed with DMF four times in the same manner as in the first washing. The resin was thus washed five times in total.

After removing the fifth washing solution, the resulting resin was subjected to Ser(tBu) elongation reaction. The elongation reaction was carried out by adding a solution obtained by mixing a 0.5 M Fmoc-Ser(tBu)-OH/0.3125 M HOOBt/NMP solution (0.18 mL) with a 10% DIC/DMF solution (0.216 mL) to the resin and shaking the mixture at 30° C. for 18 hours. The liquid phase of the elongation reaction was removed with the filter, and the resin was washed with DMF (1.0 mL) five times and then washed with DCM (1.0 mL) five times. A small amount of the resulting resin was taken from the reaction vessel, and the peptide was cleaved by adding a TFE/DCM solution (1/1 (v/v), supplemented with DIPEA) and shaking the mixture at room temperature. The solution after cleavage was analyzed by LCMS to confirm that 89% (UV area) of the target peptide (Fmoc-Ser(tBu)-MePhe-MeVal-Asp-pip (Compound 51)) and 11% (UV area) of a redundantly elongated peptide by-product (Fmoc-Ser(tBu)-Ser(tBu)-MePhe-MeVal-Asp-pip (Compound 52)) were produced.

Target Peptide (Compound 51)

Chemical formula 10

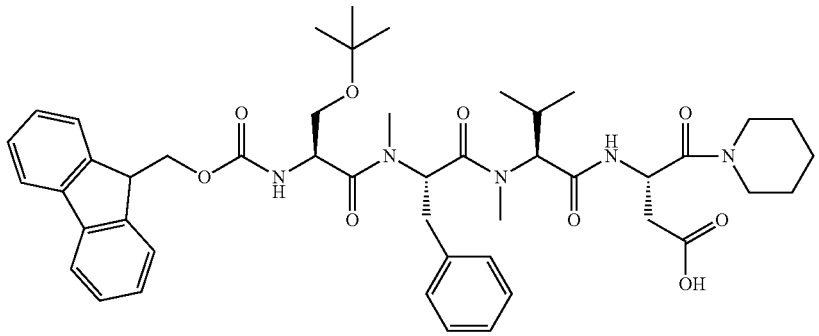

LCMS (ESI) m/z=840.4 (M+H)+
Retention time: 1.02 min (analysis condition SQDFA05)
Redundantly Elongated Peptide (Compound 52)

Chemical formula 11

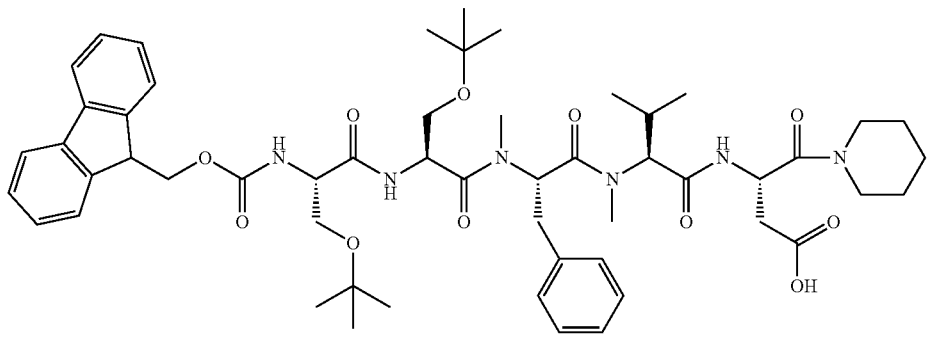

LCMS (ESI) m/z=981.5 (M−H)−
Retention time: 1.06 min (analysis condition SQDFA05)

Example 3-2: Suppressing Production of a Redundantly Elongated Peptide by Using Multiple Washing Solvents and Increasing Washing Frequency This Example confirmed that redundant elongation found during elongation using a 100 mg resin can be suppressed by using multiple washing solvents and simultaneously increasing the washing frequency.

A 100 mg portion of the prepared Fmoc-MePhe-MeVal-Asp(O-Trt(2-Cl)-resin)-pip (Compound 32: 0.448 mmol/g) was placed in a reaction vessel equipped with a filter, and the resin was swollen by adding DCM (1 mL) and shaking the mixture at room temperature for 30 minutes. After removing the DCM with the filter, the resin was washed with DMF (0.7 mL) twice. Fmoc removal was then carried out by adding a 2% DBU/DMF solution (Fmoc removal solution: 0.7 mL) to the resin and shaking the mixture at room temperature for 30 minutes. After removing the Fmoc removal solution, the first washing was conducted by adding IPA (1 mL) and shaking the mixture at room temperature for five minutes. After removing the washing solution, the resin was washed seven times in total in the same manner as in the first washing. The solvents used in the washing steps were as follows.

TABLE 4

| | Washing step | | | | | | |
|---|---|---|---|---|---|---|---|
| | 1st | 2nd | 3rd | 4th | 5th | 6th | 7th |
| Washing solvent | IPA | DCM | IPA | DCM | IPA | DMF | DMF |

After removing the seventh washing solution, the resulting resin was subjected to Ser(tBu) elongation reaction. The elongation reaction was carried out by adding a solution obtained by mixing a 0.5 M Fmoc-Ser(tBu)-OH/0.3125 M HOOBt/NMP solution (0.18 mL) with a 10% DIC/DMF solution (0.216 mL) to the resin and shaking the mixture at 30° C. for 19 hours. After removing the liquid phase of the elongation reaction with the filter, the resin was washed with DMF (1.0 mL) five times and then with DCM (1.0 mL) five times. A small amount of the resulting resin was taken from the reaction vessel, and the peptide was cleaved by adding a TFE/DCM solution (1/1 (v/v)) and shaking the mixture at room temperature. The solution after cleavage was analyzed by LCMS to confirm that the target peptide (Fmoc-Ser(tBu)-MePhe-MeVal-Asp-pip (Compound 51)) was produced and a redundantly elongated peptide by-product (Fmoc-Ser(tBu)-Ser(tBu)-MePhe-MeVal-Asp-pip (Compound 52)) was not produced.

Target Peptide (Compound 51)
LCMS (ESI) m/z=840.5 (M+H)+
Retention time: 1.02 min (analysis condition SQDFA05)

As a scaling-up study, the experiment of Example 3-3 was carried out by applying washing of seven times or more to peptide synthesis using a 1 g resin.

Example 3-3: Scaling-Up Study

This Example confirmed that redundant elongation was detected in the case of using a 1 g resin even when applying a more strict washing method in which the washing frequency is higher than in Example 3-2.

A 1.0 g portion of the prepared Fmoc-MePhe-MeVal-Asp(O-Trt(2-Cl)-resin)-pip (Compound 32: 0.448 mmol/g) was placed in a reaction vessel equipped with a filter, and the resin was swollen by adding DCM (7 mL) and shaking the mixture at room temperature for 30 minutes. After removing the DCM with the filter, the resin was washed with DMF (7 mL) twice. Fmoc removal was then carried out by adding a 2% DBU/DMF solution (Fmoc removal solution: 7.0 mL) to the resin and shaking the mixture at room temperature for 30 minutes. After removing the Fmoc removal solution, the first washing was conducted by adding IPA (7 mL) and shaking the mixture at room temperature for five minutes. After removing the washing solution, the resin was washed ten times in total in the same manner as in the first washing operation. The solvents used in the washing steps were as follows.

TABLE 5

| | Washing step | | | | | | | | | |
|---|---|---|---|---|---|---|---|---|---|---|
| | 1st | 2nd | 3rd | 4th | 5th | 6th | 7th | 8th | 9th | 10th |
| Washing solvent | IPA | DCM | IPA | DCM | IPA | DMF | IPA | DMF | DMF | DMF |

After removing the tenth washing solution, the resulting resin was subjected to Ser(tBu) elongation reaction. The elongation reaction was carried out by adding a solution obtained by mixing a 0.5 M Fmoc-Ser(tBu)-OH/0.3125 M HOOBt/NMP solution (1.8 mL) with a 10% DIC/DMF solution (2.16 mL) to the resin and shaking the mixture at 30° C. for 19 hours. After removing the liquid phase of the elongation reaction with the filter, the resin was washed with DMF (7.0 mL) five times and then with DCM (7.0 mL) five times. A small amount of the resulting resin was taken from the reaction vessel, and the peptide was cleaved by adding a TFE/DCM solution (1/1 (v/v)) and shaking the mixture at room temperature. The solution after cleavage was analyzed by LCMS to confirm that 99.92% of the target peptide (Fmoc-Ser(tBu)-MePhe-MeVal-Asp-pip (Compound 51)) was produced, while 0.08% of a redundantly elongated peptide by-product (Fmoc-Ser(tBu)-Ser(tBu)-MePhe-MeVal-Asp-pip (Compound 52)) was produced.

Target Peptide (Compound 51)
LCMS (ESI) m/z=840.3 (M+H)+
Retention time: 1.01 min (analysis condition SQDFA05)
Redundantly Elongated Peptide (Compound 52)
LCMS (ESI) m/z=981.3 (M−H)−
Retention time: 1.07 min (analysis condition SQDFA05)

From the results of Examples 3-2 and 3-3, it was found that even the washing frequency that did not cause problems in a small scale study, may not be sufficient when the peptide synthesis is scaled up or when the reaction vessel is changed. In brief, in this scaling-up experiment, the washing frequency needs to be further increased to perform elongation without causing problems of redundant elongation.

In the following Example, to provide the upper limit of the washing frequency, the Fmoc-removed resin was subjected to a washing step with triethylamine hydrochloride to inactivate the basicity of DBU used for Fmoc removal.

Example 4: Suppressing Redundant Elongation by Salt Washing

This Example confirmed that redundant elongation can be suppressed even in a 1 g resin by applying the salt washing method.

A 1.0 g portion of the prepared Fmoc-MePhe-MeVal-Asp(O-Trt(2-Cl)-resin)-pip (Compound 32: 0.448 mmol/g) was placed in a reaction vessel equipped with a filter, and the resin was swollen by adding DCM (7 mL) and shaking the mixture at room temperature for 30 minutes. After removing the DCM with the filter, the resin was washed with DMF (7 mL) twice. Fmoc removal was then carried out by adding a 2% DBU/DMF solution (Fmoc removal solution: 7.0 mL) to the resin and shaking the mixture at room temperature for 30 minutes. After removing the Fmoc removal solution, the first washing was conducted by adding IPA (7 mL) and shaking the mixture at room temperature for five minutes. After removing the washing solution, the second washing was conducted by adding Et3N.HCl (123.3 mg, 0.896 mmol) dissolved in DCM (7 mL) to the resin and shaking the mixture at room temperature for five minutes. After removing the washing solution, the third washing was conducted by adding another Et3N.HCl (123.3 mg, 0.896 mmol) dissolved in DCM (7 mL) to the resin and shaking the mixture at room temperature for five minutes again. After removing the washing solution, the fourth washing was conducted by adding DMF (7 mL) to the resin and shaking the mixture at room temperature for five minutes. After removing the washing solution, the fifth washing was conducted by adding DMF (7 mL) to the resin and shaking the mixture at room temperature for five minutes. The washing solvents and additives used in each of the washing steps were as follows.

TABLE 6

| | Washing step | | | | |
|---|---|---|---|---|---|
| | 1st | 2nd | 3rd | 4th | 5th |
| Washing solvent | IPA | DCM | DCM | DMF | DMF |
| Additive | None | Et3N•HCl | Et3N•HCl | None | None |

After removing the fifth washing solution, the resulting resin was subjected to Ser(tBu) elongation reaction. The elongation reaction was carried out by adding a solution obtained by mixing a 0.5 M Fmoc-Ser(tBu)-OH/0.3125 M HOOBt/NMP solution (1.8 mL) with a 10% DIC/DMF solution (2.16 mL) to the resin and shaking the mixture at 30° C. for 20 hours. After removing the liquid phase of the elongation reaction with the filter, the resin was washed with IPA (7.0 mL) once, with DMF (7.0 mL) four times, and then with DCM (7.0 mL) five times. A small amount of the resulting resin was taken from the reaction vessel, and the peptide was cleaved by adding a TFE/DCM solution (1/1 (v/v)) and shaking the mixture at room temperature. The solution after cleavage was analyzed by LCMS to confirm that 99.93% of the target peptide (Fmoc-Ser(tBu)-MePhe-MeVal-Asp-pip (Compound 51)) was produced, while 0.07% of a redundantly elongated peptide by-product (Fmoc-Ser(tBu)-Ser(tBu)-MePhe-MeVal-Asp-pip (Compound 52)) was produced.

Target Peptide (Compound 51)
LCMS (ESI) m/z=840.4 (M+H)+
Retention time: 1.02 min (analysis condition SQDFA05)
Redundantly Elongated Peptide (Compound 52)
LCMS (ESI) m/z=981.4 (M−H)−
Retention time: 1.07 min (analysis condition SQDFA05)

This experiment demonstrated that inactivation of the remaining DBU by washing with an Et3N.HCl solution (salt washing method) after Fmoc removal with DBU can suppress redundant elongation caused by the remaining DBU as in the case that the washing frequency was increased. Specifically, it was demonstrated that adoption of the salt washing method can reduce the washing frequency, the amount of the washing solvent, and the operational time for the washing steps after Fmoc removal.

Example 5: Comparing the Effect of Suppressing Redundant Elongation Between with or without Salt Washing In this Example, redundantly elongated peptide production was compared between the cases with or without using a triethylamine hydrochloride/dichloromethane solution (sometimes described as "salt solution") for washing of the resin after Fmoc removal with a 2% DBU/DMF solution (the total washing frequency after Fmoc removal was twice and three times).

Example 5-1: Washing Only with Organic Solvents (DCM and DMF) without Washing with a Salt Solution A 100 mg portion of the prepared Fmoc-MePhe-MeVal-Asp(O-Trt(2-Cl)-resin)-pip (Compound 32: 0.3753 mmol/g) was placed in a reaction vessel equipped with a filter, and the resin was swollen by adding dichloromethane (1 mL) and shaking the mixture at room temperature for one hour. After removing the dichloromethane with the filter, the resin was washed with DMF (0.7 mL) twice. Fmoc removal was then carried out by adding a 2% DBU/DMF solution (Fmoc removal solution: 0.7 mL) to the resin and shaking the mixture at room temperature for 10 minutes. After removing the Fmoc removal solution, the first washing was conducted by adding dichloromethane (1 mL) to the resin and shaking the mixture at room temperature for five minutes. After removing the washing solution, the second washing was conducted by adding DMF (0.7 mL) to the resin and shaking the mixture at room temperature for five minutes. After removing the washing solution, in case of conducting the third washing, DMF (0.7 mL) was added to the resin, the resin was shaken at room temperature for five minutes, and the washing solution was removed.

The resulting resin was subjected to Ser(tBu) elongation reaction. The elongation reaction was carried out by adding a solution obtained by mixing a 0.6 M Fmoc-Ser(tBu)-OH/0.375 M HOAt/NMP solution (0.3 mL) with a 10% DIC/DMF solution (0.36 mL) to the resin and shaking the mixture at 40° C. for 2.5 hours. After removing the liquid phase of the elongation reaction with the filter, the resin was washed with DMF (0.7 mL) four times and washed with dichloromethane (0.7 mL) four times. The peptide was cleaved by treating the resulting resin with a TFE/DCM solution (1/1 (v/v)). The solution after cleavage was analyzed by LCMS and the results are as follows: Production of the target peptide (Fmoc-Ser(tBu)-MePhe-MeVal-Asp-pip (Compound 51)) and also a redundantly elongated peptide (Fmoc-Ser(tBu)-Ser(tBu)-MePhe-MeVal-Asp-pip (Compound 52)) was detected.

TABLE 7

| Washing frequency after Fmoc removal | Target peptide (Compound 51) | Redundantly elongated peptide (Compound 52) |
| --- | --- | --- |
| Twice | 96.3% | 3.7% |
| Three times | 97.2% | 2.8% |

Target Peptide (Compound 51)
LCMS (ESI) m/z=840.5 (M+H)+
Retention time: 1.02 min (analysis condition SQDFA05)
Redundantly Elongated Peptide (Compound 52)
LCMS (ESI) m/z=981.5 (M−H)−
Retention time: 1.06 min (analysis condition SQDFA05)

Example 5-2: Washing with a 0.08 M Triethylamine Hydrochloride/Dichloromethane Solution A 100 mg portion of the prepared Fmoc-MePhe-MeVal-Asp(O-Trt(2-Cl)-resin)-pip (Compound 32: 0.3753 mmol/g) was placed in a reaction vessel equipped with a filter, and the resin was swollen by adding dichloromethane (1 mL) and shaking the mixture at room temperature for one hour. After removing the dichloromethane with the filter, the resin was washed with DMF (0.7 mL) twice. Fmoc removal was then carried out by adding a 2% DBU/DMF solution (Fmoc removal solution: 0.7 mL) to the resin and shaking the mixture at room temperature for 10 minutes. After removing the Fmoc removal solution, the first washing was conducted by adding a 0.08 M triethylamine hydrochloride/dichloromethane solution (1 mL) to the resin and shaking the mixture at room temperature for five minutes. After removing the washing solution, the second washing was conducted by adding DMF (0.7 mL) to the resin and shaking the mixture at room temperature for five minutes. After removing the washing solution, in case of conducting the third washing, DMF (0.7 mL) was added to the resin, the resin was shaken at room temperature for five minutes, and the washing solution was removed. The resulting resin was subjected to Ser(tBu) elongation reaction.

The elongation reaction was carried out by adding a solution obtained by mixing a 0.6 M Fmoc-Ser(tBu)-OH/0.375 M HOAt/NMP solution (0.3 mL) with a 10% DIC/DMF solution (0.36 mL) to the resin and shaking the mixture at 40° C. for 2.5 hours. After removing the liquid phase of the elongation reaction with the filter, the resin was washed with DMF (0.7 mL) four times and washed with dichloromethane (0.7 mL) four times. The peptide was cleaved from the resulting resin with a TFE/DCM solution (1/1 (v/v)). The solution after cleavage was analyzed by LCMS to confirm that only the target peptide (Fmoc-Ser(tBu)-MePhe-MeVal-Asp-pip (Compound 51)) was detected and a redundantly elongated peptide (Fmoc-Ser(tBu)-Ser(tBu)-MePhe-MeVal-Asp-pip (Compound 52)) was not detected.

TABLE 8

| Washing frequency after Fmoc removal | Target peptide (Compound 51) | Redundantly elongated peptide (Compound 52) |
| --- | --- | --- |
| Twice (the first washing being salt washing) | >99.5% | N.D. |
| Three times (the first washing being salt washing) | >99.5% | N.D. |

N.D. = Not detected

As described above, in the washing steps for the Fmoc-removed resin, 2.8% of the redundantly elongated peptide was confirmed to be produced even after washing three times when the resin was washed only with organic solvents without performing salt washing, while the redundantly elongated peptide was not produced and only the target peptide was obtained in a high purity even after washing twice when salt washing was performed. It was confirmed that high-purity peptides can be obtained while reducing the washing frequency by applying the salt washing method to washing steps after Fmoc removal.

Example 6: Studying the Type of Acids Forming Salts with Bases and the Type of Solvents This Example confirmed the washing effect when using solutions of various salts formed of bases and acids (sometimes described as "salt solutions") for washing of the resin after Fmoc removal with a 2% DBU/DMF solution.

Example 6-1: Washing with a Solution Obtained by Dissolving a Salt Formed of DIPEA and an Acid A 100 mg portion of the prepared Fmoc-MePhe-MeVal-Asp(O-Trt(2-Cl)-resin)-pip (compound 32: 0.3753 mmol/g) was placed in a reaction vessel equipped with a filter, and the resin was swollen by adding dichloromethane (1 mL) and shaking the mixture at room temperature for one hour. After removing the dichloromethane with the filter, the resin was washed with DMF (0.7 mL) twice. Fmoc removal was then carried out by adding a 2% DBU/DMF solution (Fmoc removal solution: 0.7 mL) to the resin and shaking the mixture at room temperature for 10 minutes. After removing the Fmoc removal solution, the first washing was conducted by adding a solution of a salt and an organic solvent shown in the following table (each 0.08 M, 1 mL) to the resin and shaking the mixture at room temperature for five minutes. After removing the washing solution, the second washing was conducted by adding DMF (0.7 mL) to the resin and shaking the mixture at room temperature for five minutes. After removing the washing solution, the resulting resin was subjected to Ser(tBu) elongation reaction.

The elongation reaction was carried out by adding a solution obtained by mixing a 0.6 M Fmoc-Ser(tBu)-OH/0.375 M HOAt/NMP solution (0.3 mL) with a 10% DIC/DMF solution (0.36 mL) to the resin and shaking the mixture at 40° C. for 2.5 hours. After removing the liquid phase of the elongation reaction with the filter, the resin was washed with DMF (0.7 mL) four times and washed with dichloromethane (0.7 mL) four times. The peptide was cleaved by treating the resulting resin with a TFE/DCM solution (1/1 (v/v)). The solution after cleavage was analyzed by LCMS to find that in all cases a redundantly elongated peptide (Fmoc-Ser(tBu)-Ser(tBu)-MePhe-MeVal-Asp-pip (Compound 52)) was not produced and only the target peptide (Fmoc-Ser(tBu)-MePhe-MeVal-Asp-pip (Compound 51)) was obtained in a high purity. From the results, it was confirmed that various types of acids can be used as salt-forming acids and various solvents can also be used.

TABLE 9

| Type of salt solution | Target peptide (Compound 51) | Redundantly elongated peptide (Compound 52) |
| --- | --- | --- |
| DIPEA•HCl/DCM | >99.5% | N.D. |
| DIPEA•TsOH/DCM | >99.5% | N.D. |
| DIPEA•HOAt/DCM | >99.5% | N.D. |
| DIPEA•oxyma/DCM | >99.5% | N.D. |
| DIPEA•HOBt/DCM | >99.5% | N.D. |
| DIPEA•HCl/DMF | >99.5% | N.D. |
| DIPEA•TsOH/DMF | >99.5% | N.D. |
| DIPEA•HOAt/DMF | >99.5% | N.D. |
| DIPEA•oxyma/DMF | >99.5% | N.D. |

Example 6-2: Studying a Method of Forming a Salt in a Solvent

In this Example, a salt solution was prepared not by dissolving a previously prepared salt in a solvent, but by dissolving a base (2,4,6-trimethylpyridine) and an acid (oxyma) individually in a solvent, and washing was performed.

After sequentially dissolving 2,4,6-Trimethylpyridine (2,4,6-collidine) (121.2 mg) and oxyma (142.1 mg) in DMF (about 10 mL), DMF was added so that the total volume of the solution became 12 mL. A 0.08 M 2,4,6-trimethylpyridine oxyma salt/DMF solution was thus prepared.

A 100 mg portion of the prepared Fmoc-MePhe-MeVal-Asp(O-Trt(2-Cl)-resin)-pip (Compound 32: 0.3753 mmol/g) was placed in a reaction vessel equipped with a filter, and the resin was swollen by adding dichloromethane (1 mL) and shaking the mixture at room temperature for one hour. After removing the dichloromethane with the filter, the resin was washed with DMF (0.7 mL) twice. Fmoc removal was then carried out by adding a 2% DBU/DMF solution (Fmoc removal solution: 0.7 mL) to the resin and shaking the mixture at room temperature for 10 minutes. After removing the Fmoc removal solution, the first washing was conducted by adding the prepared 0.08 M 2,4,6-trimethylpyridine oxyma salt/DMF solution (1 mL) to the resin and shaking the mixture at room temperature for five minutes. After removing the washing solution, the second washing was conducted by adding DMF (0.7 mL) to the resin and shaking the mixture at room temperature for five minutes. After removing the washing solution, the resulting resin was subjected to Ser(tBu) elongation reaction.

The elongation reaction was carried out by adding a solution obtained by mixing a 0.6 M Fmoc-Ser(tBu)-OH/0.375 M HOAt/NMP solution (0.3 mL) with a 10% DIC/DMF solution (0.36 mL) to the resin and shaking the mixture at 40° C. for 2.5 hours. After removing the liquid phase of the elongation reaction with the filter, the resin was washed with DMF (0.7 mL) four times and the unreacted point was capped. The capping was carried out by adding a solution obtained by mixing a 0.6 M Fmoc-Gly-OH/0.375 M HOAt/NMP solution (0.3 mL) with a 10% DIC/DMF solution (0.36 mL) to the resin and shaking the mixture at 40° C. for 14 hours. After removing the liquid phase of the capping solution with the filter, the resin was washed with DMF (0.7 mL) four times and washed with dichloromethane (0.7 mL) four times. The peptide was cleaved by treating the resulting resin with a TFE/DCM solution (1/1 (v/v)). The solution after cleavage was analyzed by LCMS to find that production of a redundantly elongated peptide (Fmoc-Ser(tBu)-Ser(tBu)-MePhe-MeVal-Asp-pip (Compound 52)) was not detected, a product capped with Fmoc-Gly-OH (Fmoc-Gly-MePhe-MeVal-Asp-pip (Compound 53)) was also not detected, and only the target peptide (Fmoc-Ser(tBu)-MePhe-MeVal-Asp-pip (Compound 51)) was obtained in a high purity. From the results it was confirmed that production of redundantly elongated peptides can be suppressed and high-purity peptides can be obtained by dissolving a base and an acid individually in a solvent, and forming a salt in the solvent, without preparing a salt in advance.

Example 6-3: Washing with a 0.08 M Pyridine Hydrochloride/Dichloromethane Solution A 100 mg portion of the prepared Fmoc-MePhe-MeVal-Asp(O-Trt(2-Cl)-resin)-pip (Compound 32: 0.3753 mmol/g) was placed in a reaction vessel equipped with a filter, and the resin was swollen by adding dichloromethane (1 mL) and shaking the mixture at room temperature for one hour. After removing the dichloromethane with the filter, the resin was washed with DMF (0.7 mL) twice. Fmoc removal was then carried out by adding a 2% DBU/DMF solution (Fmoc removal solution: 0.7 mL) to the resin and shaking the mixture at room temperature for 10 minutes. After removing the Fmoc removal solution, the first washing was conducted by adding a 0.08 M pyridine hydrochloride/dichloromethane solution (1 mL) to the resin and shaking the mixture at room temperature for five minutes. After removing the washing solution, the second washing was conducted by adding DMF (0.7 mL) to the resin and shaking the mixture at room temperature for five minutes. After removing the washing solution, the resulting resin was subjected to Ser(tBu) elongation reaction. The elongation reaction was carried out by adding a solution obtained by mixing a 0.6 M Fmoc-Ser (tBu)-OH/0.375 M HOAt/NMP solution (0.3 mL) with a 10% DIC/DMF solution (0.36 mL) to the resin and shaking the mixture at 40° C. for 2.5 hours.

After removing the liquid phase of the elongation reaction with the filter, the resin was washed with DMF (0.7 mL) four times and the unreacted point was capped. The capping was carried out by adding a solution obtained by mixing a 0.6 M Fmoc-Gly-OH/0.375 M HOAt/NMP solution (0.3 mL) with a 10% DIC/DMF solution (0.36 mL) to the resin and shaking the mixture at 40° C. for 14 hours. After removing the liquid phase of the capping solution with the filter, the resin was washed with DMF (0.7 mL) four times and with dichloromethane (0.7 mL) four times. The peptide was cleaved by treating the resulting resin with a TFE/DCM solution (1/1 (v/v)). The solution after cleavage was analyzed by LCMS to find that a redundantly elongated peptide (Fmoc-Ser(tBu)-Ser(tBu)-MePhe-MeVal-Asp-pip (Compound 52)) was not observed, but production of the target peptide (Fmoc-Ser(tBu)-MePhe-MeVal-Asp-pip (Compound 51)) reached only 80.3%, and 17.4% of a peptide capped with Fmoc-Gly (Fmoc-Gly-MePhe-MeVal-Asp-pip (Compound 53)) was produced.

Peptide Capped with Fmoc-Gly (Compound 53)

was added so that the total volume of the solution became 12 mL. A 0.08 M DIPEA.HFIP salt/DMF solution was thus prepared.

A 100 mg portion of the prepared Fmoc-MePhe-MeVal-Asp(O-Trt(2-Cl)-resin)-pip (Compound 32: 0.3753 mmol/g) was placed in a reaction vessel equipped with a filter, and the resin was swollen by adding dichloromethane (1 mL) and shaking the mixture at room temperature for one hour. After removing the dichloromethane with the filter, the resin was washed with DMF (0.7 mL) twice. Fmoc removal was then carried out by adding a 2% DBU/DMF solution (Fmoc removal solution: 0.7 mL) to the resin and shaking the mixture at room temperature for five minutes. After removing the Fmoc removal solution, the first washing was conducted by adding the prepared 0.08 M DIPEA.HFIP salt/DMF solution (1 mL) to the resin and shaking the mixture at room temperature for five minutes. After removing the washing solution, the second washing was conducted by adding DMF (0.7 mL) to the resin and shaking the mixture at room temperature for five minutes. After removing the washing solution, the resulting resin was subjected to Ser(tBu) elongation reaction.

The elongation reaction was carried out by adding a solution obtained by mixing a 0.6 M Fmoc-Ser(tBu)-OH/0.375 M HOAt/NMP solution (0.3 mL) with a 10% DIC/DMF solution (0.36 mL) to the resin and shaking the mixture at 40° C. for 2.5 hours. After removing the liquid phase of the elongation reaction with the filter, the resin was washed with DMF (0.7 mL) four times and then washed with dichloromethane (0.7 mL) four times. The peptide was cleaved by treating the resulting resin with a TFE/DCM solution (1/1 (v/v)). The solution after cleavage was analyzed by LCMS to confirm that 97.91% (LC UVarea) of the target peptide (Fmoc-Ser(tBu)-MePhe-MeVal-Asp-pip (Compound 51)) was produced, while 2.09% (LC UVarea)

Chemical formula 12

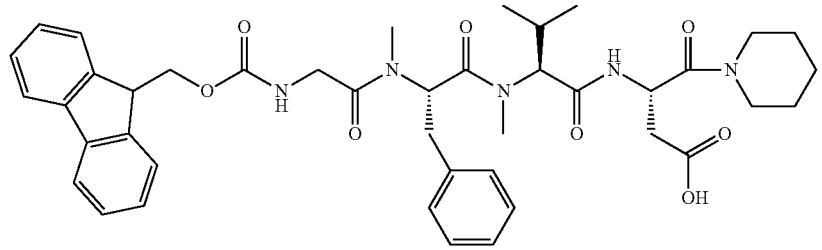

LCMS (ESI) m/z=754.4 (M+H)+

Retention time: 0.92 min (analysis condition SQDFA05)

The conjugate acid of pyridine is reported to have a pKa of 5.21 (D. H. Ripin, D. A. Evans, pKa's of Nitrogen Acids, [online], [retrieved on Dec. 5, 2017], internet <URL: http://evans.rc.fas.harvard.edu/pdf/evans_pKa_table.pdf5). Without being intended to be bound to any particular theory, it was suggested that because of salt washing, salt formation proceeded with not only the remaining DBU but also the amino group exposed at the N-terminus and the reaction rate was decreased.

Example 6-4: Washing with a 0.08 M DIPEA.HFIP Salt/DMF Solution

DIPEA (DIEA) (129.3 mg) and HFIP (168.0 mg) were sequentially dissolved in DMF (about 10 mL), and DMF of a redundantly elongated peptide (Fmoc-Ser(tBu)-Ser(tBu)-MePhe-MeVal-Asp-pip (Compound 52)) was produced. Only the target peptide (Fmoc-Ser(tBu)-MePhe-MeVal-Asp-pip (Compound 51)) was obtained in a high purity.

As known from the literature, HFIP has a pKa value of 9.3 (Tetrahedron Asymmetry, 2012, 23, 1023-1027). In salt washing, salt-forming acids having a pKa value of at most 9 were demonstrated to be insufficient for inactivating the remaining DBU.

Example 7: Scaled-Up Peptide Synthesis to which the Salt Washing Method is Applied (where the Salt Washing Method is Applied to all Fmoc Removal Steps and a 60 g Resin is Used) Fmoc Removal Step A 60 g portion of the prepared Fmoc-Asp(O-Trt(2-Cl)-resin)-pip (Compound 31: 0.461 mmol/g) was placed in a reaction vessel equipped with a filter, and the resin was swollen by adding DCM (600 mL) and shaking the mixture at room temperature for 30 minutes. After removing the DCM with the filter, the resin was washed with DMF (600 mL) twice. Fmoc removal was then carried out by adding a 2% DBU/DMF solution (Fmoc removal solution: 420 mL) to the resin and shaking the mixture at room temperature for 30 minutes. After removing the Fmoc removal solution, the first washing was conducted by adding IPA (420 mL) and shaking the mixture at room temperature for five minutes. After removing the washing solution, the second washing was conducted by adding Et3N.HCl (7.61 g, 55.3 mmol) dissolved in DCM (420 mL) to the resin and shaking the mixture at room temperature for five minutes. After removing the washing solution, the third washing was conducted by adding another Et3N.HCl (7.61 g, 55.3 mmol) dissolved in DCM (420 mL) to the resin and shaking the mixture at room temperature for five minutes again. After removing the washing solution, the fourth washing was conducted by adding DMF (420 mL) to the resin and shaking the mixture at room temperature for five minutes. After removing the washing solution, the fifth washing was conducted by adding DMF (420 mL) to the resin and shaking the mixture at room temperature for five minutes. After removing the washing solution, the resulting resin was subjected to MePhe elongation reaction.

Elongation Step

The elongation reaction was carried out by adding a solution obtained by mixing a 0.5 M Fmoc-MePhe-OH/0.3125 M HOAt/NMP solution (110.8 mL) with a 10% DIC/DMF solution (134.2 mL) to the resin and shaking the mixture at 30° C. for 13 hours. After removing the liquid phase of the elongation reaction with the filter, the resin was washed four times with IPA (420 mL), DMF (420 mL), IPA (420 mL), and DMF (420 mL) and then washed with DCM (420 mL) three times.

To confirm the reaction conversion rate, a small amount of the resin (about 100 mg) was taken from the reaction vessel, swollen with DCM, and washed with DMF twice, and the unreacted point was capped. The capping was carried out by adding a solution obtained by mixing a 0.6 M Fmoc-Gly-OH/0.375 M HOAt/NMP solution (0.3 mL) with a 10% DIC/DMF solution (0.36 mL) to the resin and shaking the mixture at room temperature for one hour. After removing the liquid phase of the capping solution with the filter, the resin was washed four times with IPA, DMF, IPA, and DMF and then washed with DCM three times.

The peptide was washed by adding a TFE/DCM solution (1/1 (v/v)) to the resulting resin and shaking the mixture at room temperature. The solution after cleavage was analyzed by LCMS to confirm that the target peptide (Fmoc-MePhe-Asp-pip (Compound 54)) was produced. Meanwhile, a non-elongated peptide (Fmoc-Gly-Asp-pip (Compound 55)) which did not undergo the intended elongation and was capped with Fmoc-Gly-OH at its N-terminus was not observed.

Target Peptide (Compound 54)

Chemical formula 13

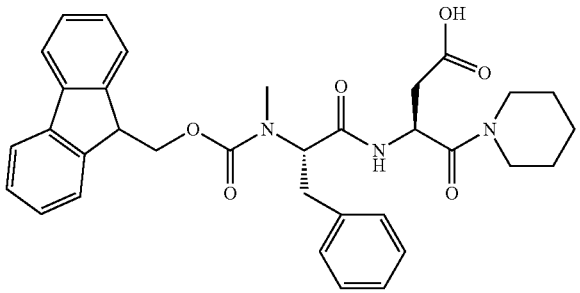

LCMS (ESI) m/z=584.2 (M+H)+

Retention time: 0.89 min (analysis condition SQDFA05)

Non-Elongated Peptide Capped with Fmoc-Gly (Compound 55)

Chemical formula 14

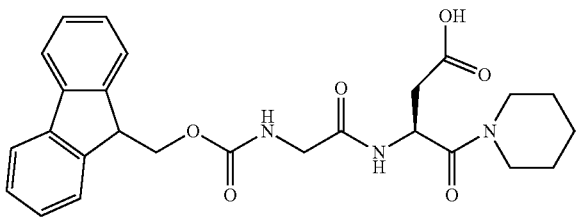

The target peptide D-Ala-MeLeu-MeAla-MePhe-Ser(tBu)-MePhe-Leu-MeLeu-Thr(THP)-MePhe-Asp-pip (Compound 56) was confirmed to be produced by similarly repeating the Fmoc removal step and the elongation step to elongate the peptide, removing the N-terminal Fmoc group, and then cleaving the peptide from the resin using TFE/DCM (1/1 (v/v)). The types of the amino acids and the additives, the reaction temperatures, and the reaction times used in each of the elongation steps were as follows. The conversion rate was calculated by the following equation.

Conversion rate (%)=(LC UVarea % of the peak of the peptide with the target Fmoc amino acid introduced)×100/{(LC UVarea % of the peak of the target peptide with the target Fmoc amino acid introduced)+(LC UVarea % of the peak of the peptide in which the unreacted point is capped with Fmoc-Gly)}  (Equation 1)

Target Peptide (Compound 56)

Chemical formula 15

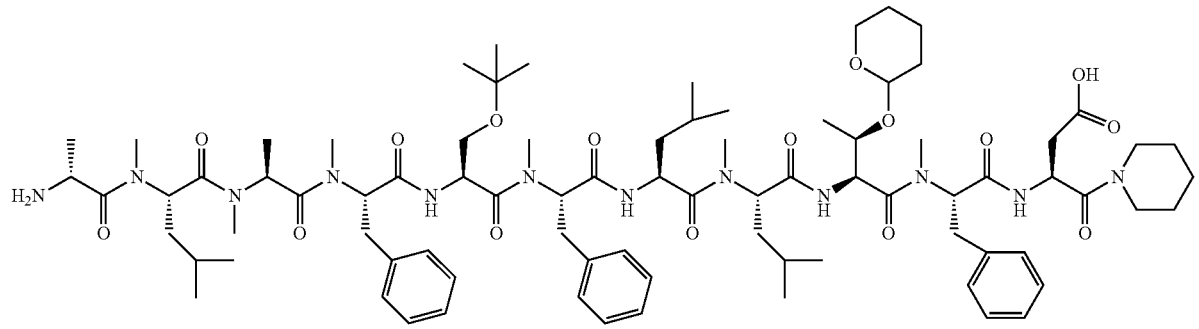

LCMS (ESI) m/z=1535.9 (M+H)+

Retention time: 0.81 min (analysis condition SQDFA05)

TABLE 10

| Elongation step | Amino acid used for elongation | Additive | Reaction temperature (° C.) | Reaction time (h) | Conversion ratio |
|---|---|---|---|---|---|
| 1 | MePhe | HOAt | 30 | 13 | 100% |
| 2 | Thr(THP) | HOAt | 30 | 16 | 100% |
| 3 | MeLeu | HOAt | 30 | 15.5 | 100% |
| 4 | Leu | HOAt | 30 | 13 | 100% |
| 5 | MePhe | HOAt | 30 | 14.5 | 100% |
| 6 | Ser(tBu) | HOAt | 30 | 14 | 100% |
| 7 | MePhe | HOAt | 30 | 15 | 100% |
| 8 | MeAla | HOAt | 30 | 14 | 100% |

TABLE 10-continued

| Elongation step | Amino acid used for elongation | Additive | Reaction temperature (° C.) | Reaction time (h) | Conversion ratio |
|---|---|---|---|---|---|
| 9 | MeLeu | HOAt | 30 | 14 | 100% |
| 10 | D-Ala | HOAt | 30 | 13 | 100% |

In this synthesis, a redundantly elongated peptide was not detected in each elongation step. Therefore, it was confirmed that the salt washing method of the present disclosure can be applied irrespective of the type of the amino acids used for elongation. The method was also shown to be a technique effective for scaled-up synthesis of high-purity peptides.

The peptide (Compound 56) obtained in the above-described elongation was cleaved from the resin, cyclized, deprotected, and reverse-phase purified according to the following scheme to provide a cyclized peptide (Compound 57, 7.08 g, 98.05% purity (UV area)).

Chemical formula 16

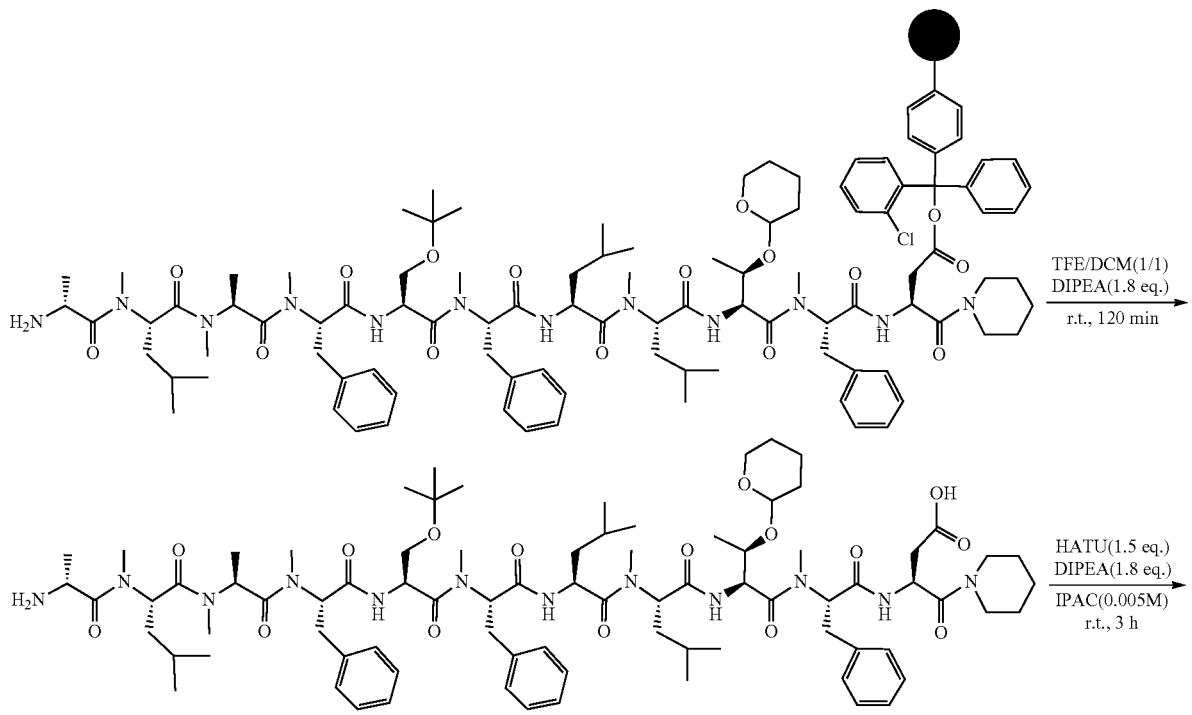

-continued
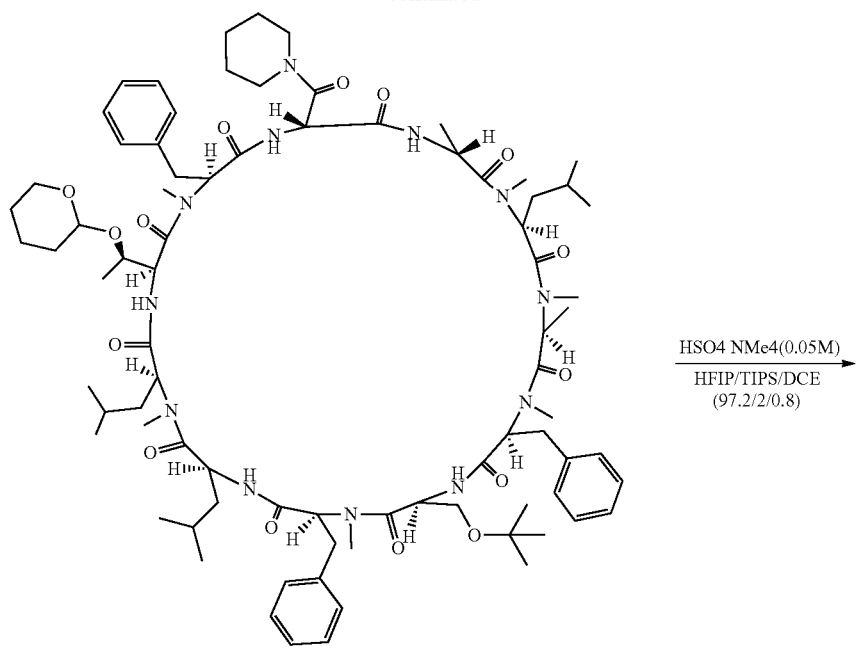
HSO4 NMe4(0.05M)
HFIP/TIPS/DCE
(97.2/2/0.8)
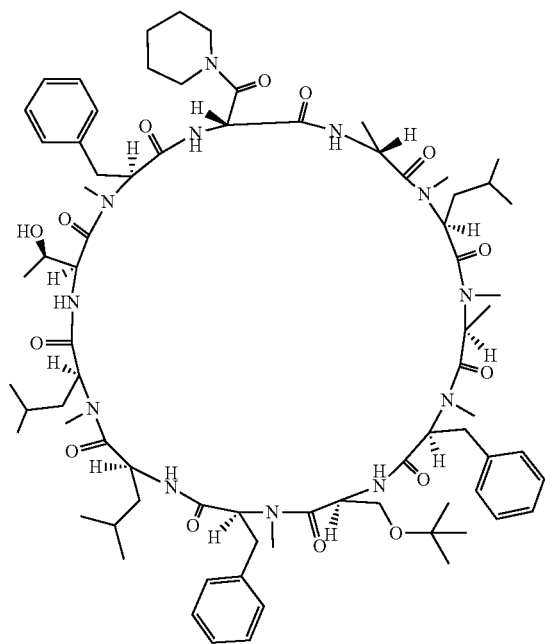

Cyclized Peptide (Compound 57)

Chemical formula 17

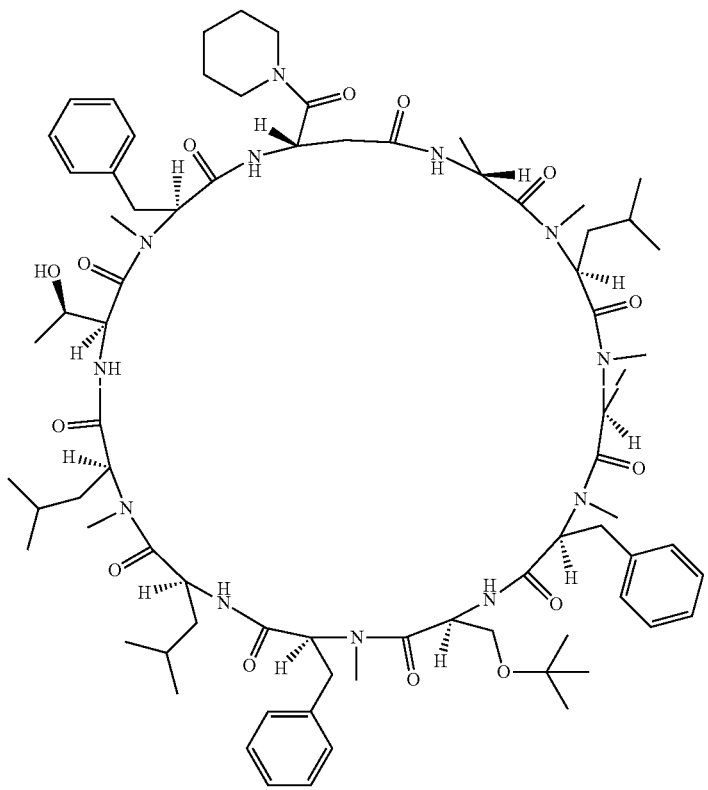

LCMS (ESI) m/z=1433.9 (M+H)+
Retention time: 0.76 min (analysis condition SQDFA50)

INDUSTRIAL APPLICABILITY

The present invention relates to methods of producing peptides, methods of treating bases for use in the methods of producing peptides, inactivating agents for bases for use in the same, and such. The present invention is useful for, for example, shortening the production time and the equipment utilization time and reducing costs in chemical peptide synthesis. The present invention is also useful for, for example, reducing by-products and increasing the purity of target peptides.

The invention claimed is:
1. A method of producing a peptide, the method comprising the steps of:
   (a) inactivating a base X by allowing the base X, an amino group-containing compound, and a salt formed of a base Y and an acid Z to coexist, wherein the base X is a deprotecting agent; and
   (b) after the step (a), elongating a peptide chain by allowing the amino group-containing compound and an amino acid or peptide having an amino group protected by a protecting group P to coexist to thereby elongate the peptide chain;
wherein a conjugate acid of the base Y has a pKa smaller than that of a conjugate acid of the base X, and the acid Z is an acid having a pKa of 5.0 or less,
wherein the base X is selected from DBU, piperidine, DBN, 7-methyl-1,5,7-triazabicyclo[4.4.0]dec-5-ene, pyrrolidine, morpholine, 1,1,3,3-tetramethylguanidine, and 1,5,7-triazabicyclo[4.4.0]dec-5-ene;
wherein the base Y is selected from triethylamine, N,N-diisopropylethylamine, trimethylamine, tributylamine, pyridine, 2,6-dimethylpyridine, and 2,4,6-trimethylpyridine; and
wherein the amino group-containing compound is an amino acid or peptide having at least one free primary amino group or free secondary amino group.

2. The method according to claim 1, further comprising, prior to the step (a), the step of:
   (a') removing with the base X a protecting group Q of the amino group-containing compound protected by the protecting group Q.

3. The method according to claim 1, wherein the protecting group P is removable with a base.

4. The method according to claim 3, wherein the protecting group removable with a base is a protecting group having an Fmoc backbone.

5. The method according to claim 1, wherein the amino group-containing compound is (i) an amino group-containing compound attached to a solid-phase support or (ii) an amino group-containing compound having a carboxy group protected by a protecting group.

6. The method according to claim 2, wherein the steps (a') to (b) are repeated twice or more.

7. The method according to claim 1, further comprising after step (b) adding an inactivating agent for base X, wherein the inactivating agent comprises a salt formed of the base Y and the acid Z.

8. The method according to claim 2, wherein the protecting groups P and Q are removable with a base.

9. The method according to claim 2, further comprising after step (b) adding an inactivating agent for base X, wherein the inactivating agent comprises a salt formed of the base Y and the acid Z.

10. The method according to claim 1, wherein the conjugate acid of the base X has a pKa of 10.0 or more.

11. The method according to claim 1, wherein the base X is DBU or DBN.

12. The method according to claim 1, wherein the base X is DBU.

13. The method according to claim 1, wherein the base Y is triethylamine, N,N-diisopropylethylamine, pyridine, or 2,6-dimethylpyridine.

14. The method according to claim 1, wherein the base Y is triethylamine or N,N-diisopropylethylamine.

15. The method according to claim 5, further comprising, after the step (b), the step of:
(c) cleaving the peptide from the solid-phase support.

16. The method according to claim 15, wherein the solid-phase support is a polymer.

17. The method according to claim 8, wherein the protecting groups P and Q are protecting groups having an Fmoc backbone.

18. The method according to claim 11, wherein the base Y is triethylamine, N,N-diisopropylethylamine, pyridine, or 2,6-dimethylpyridine.

19. The method according to claim 18, wherein the base Y is triethylamine or N,N-diisopropylethylamine.

20. The method according to claim 19, wherein the acid Z is selected from HCl, TsOH, HOAt, HOBt, or oxyma.

21. The method according to claim 12, wherein the base Y is triethylamine, N,N-diisopropylethylamine, pyridine, or 2,6-dimethylpyridine.

22. The method according to claim 21, wherein the base Y is triethylamine or N,N-diisopropylethylamine.

23. The method according to claim 22, wherein the acid Z is selected from HCl, TsOH, HOAt, HOBt, or oxyma.

* * * * *